(12) United States Patent
Matier et al.

(10) Patent No.: US 7,678,829 B2
(45) Date of Patent: Mar. 16, 2010

(54) OCULOSELECTIVE DRUGS AND PRODRUGS

(75) Inventors: William L. Matier, Hockessin, DE (US); Ghanshyam Patil, Lincoln University, PA (US)

(73) Assignee: QLT Inc., Vancouver, BC (CA)

( * ) Notice: Subject to any disclaimer, the term of this patent is extended or adjusted under 35 U.S.C. 154(b) by 1109 days.

(21) Appl. No.: 11/136,625

(22) Filed: May 24, 2005

(65) Prior Publication Data

US 2006/0019955 A1 Jan. 26, 2006

Related U.S. Application Data

(60) Provisional application No. 60/574,157, filed on May 25, 2004.

(51) Int. Cl.
- C07D 307/08 (2006.01)
- A61K 31/34 (2006.01)
- A61K 31/215 (2006.01)

(52) U.S. Cl. .................. 514/461; 514/531; 549/429

(58) Field of Classification Search .......... 560/155, 560/157; 514/565, 531, 461, 408; 549/429
See application file for complete search history.

(56) References Cited

U.S. PATENT DOCUMENTS

| | | | |
|---|---|---|---|
| 4,195,085 A | 3/1980 | Stone | 424/248.51 |
| 4,228,169 A | 10/1980 | Johnson et al. | 424/258 |
| 4,260,764 A | 4/1981 | Johnson | 546/153 |
| 4,309,545 A | 1/1982 | Johnson | 546/108 |
| 4,402,974 A | 9/1983 | Matier et al. | 424/308 |
| 4,454,154 A | 6/1984 | Matier | 424/309 |
| 4,455,317 A | 6/1984 | Matier | 424/309 |
| 4,461,904 A | 7/1984 | York, Jr. | 548/315 |
| 4,515,800 A | 5/1985 | Cavero et al. | 514/392 |
| 4,517,199 A | 5/1985 | York, Jr. | 514/392 |
| 4,897,417 A | 1/1990 | Patil et al. | 514/461 |
| 4,966,914 A | 10/1990 | Patil et al. | 514/461 |
| 5,459,140 A | 10/1995 | Gramer | 514/236.2 |
| 5,466,233 A | 11/1995 | Weiner et al. | 604/890.1 |
| 5,502,052 A | 3/1996 | DeSantis | 514/236.2 |
| 5,532,237 A | 7/1996 | Gallant et al. | 514/435.2 |
| 5,536,749 A | 7/1996 | Matier et al. | |
| 5,605,906 A | 2/1997 | Lau | 514/298 |
| 5,707,643 A | 1/1998 | Ogura et al. | 424/428 |
| 5,718,922 A | 2/1998 | Herrero-Vanrell et al. | 424/501 |

(Continued)

FOREIGN PATENT DOCUMENTS

BE 854655 11/1977

OTHER PUBLICATIONS

Boger, W.P., "The treatment of glaucoma: role of β-blocking agents," *Drugs*, 1979, 18, 25-32.

(Continued)

*Primary Examiner*—Taylor Victor Oh
(74) *Attorney, Agent, or Firm*—Pillsbury Winthrop Shaw Pittman LLP

(57) ABSTRACT

Compounds of the following formula are disclosed:

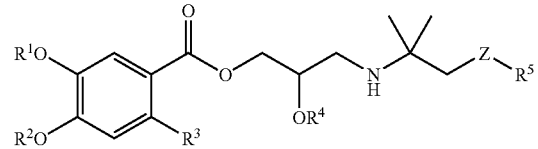

Methods of preparing the compounds, pharmaceutical compositions comprising the compounds, and methods of treating patients by administration of the pharmaceutical compositions, are also disclosed.

62 Claims, 2 Drawing Sheets

U.S. PATENT DOCUMENTS

| | | | | |
|---|---|---|---|---|
| 5,869,079 | A | 2/1999 | Wong et al. | 424/426 |
| 5,902,598 | A | 5/1999 | Chen et al. | 424/423 |
| 6,154,671 | A | 11/2000 | Parel et al. | 604/20 |
| 6,251,090 | B1 | 6/2001 | Avery et al. | 604/9 |
| 6,331,313 | B1 | 12/2001 | Wong et al. | 424/427 |
| 6,375,972 | B1 | 4/2002 | Guo et al. | 44/423 |

OTHER PUBLICATIONS

Bundgaard, H., et al., "Timolol prodrugs: synthesis, stability and lipophilicity of various alkyl, cycloalkyl and aromatic esters of timolol," *Int'l. J. of Pharmaceutics*, 1988, 46, 77-88.

Burstein, N.L., et al., "Review: corneal penetration and ocular bioavailability of drugs," *J. of Ocular Pharmacol.*, 1985, 1(3), 309-326.

Dewley, W.L., "Cannabinoid pharmacology," *Pharmac. Rev.*, 1986, 38(2), 151-177.

Feve, B., et al., "Transcriptional down-regulation by insulin of the $\beta_3$-adrenergic receptor expression in 3T3-F442A adipocytes: a mechanism for repressing the cAMP signaling pathway," *Proc. Natl. Acad. Sci. USA*, 1994, 91, 5677-5681.

Greene, T.W., et al., "Protection for the hydroxyl group, including 1,2- and 1,3-diols," *Chapter 2* and "Protection for phenols and catechols," *Chapter 3*, Protective Groups in Organic Synthesis, 2$^{nd}$ Ed., *John Wiley & Sons*, NY, 1991, 10-174.

Hovgaard, L., et al., "Drug delivery studies in Caco-2 monolayers. Synthesis, hydrolysis, and transport of O-cyclopropane carboxylic acid ester prodrugs of various $\beta$-blocking agents," *Pharm. Res.*, 1995, 12(3), 387-392.

Huh, P.W., et al., "Neuroprotection by LY341122, a novel inhibitor of lipid peroxidation, against focal ischemic brain damage in rats," *Eur. J. of Pharmacol.*, 2000, 389, 79-88.

Jordan, C.G., "How an increase in the carbon chain length of the ester moiety affects the stability of a homologous series of oxprenolol esters in the presence of biological enzymes," *J. of Pharm. Sci.*, 1998, 87(7), 880-885.

Lee, V.H.L., et al., "Improved ocular drug delivery with prodrugs," *Marcel Dekker, Inc.*, Sloan, K.B. (Ed.), 1992, Chapter 7, 221-297.

McGuinness, R., et al., "Timolol and dipivalyl epinephrine combination therapy," *Australian J. of Ophthalmol.*, 1982, 10, 179-182.

Mousa, S.A., et al., "Myocardial anti-ischemic characteristics of a novel class of $\beta$-adrenoceptor blockers," *Int. J. Clin. Pharmacol. Therap. Toxicol.*, 1992, 30(3), 103-106.

Munro, S., et al., "Molecular characterization of a peripheral receptor for cannabinoids," *Nature*, 1993, 365, 61-65.

Shameem, M., et al., "An in-vitro and in-vivo correlative approach to the evaluation of ester prodrugs to improve oral delivery of propranolol," *J. Pharm. Pharmacol.*, 1993, 45, 246-252.

Weinreb, R.N., et al., "Effect of adding betaxolol to dipivefrin therapy," *Am. J. of Ophthalmol.*, 1986, 101, 196-198.

Zimmerman, T.J., et al., "The beta-adrenergic blocking agents and the treatment of glaucoma," *Survey of Ophthalmol.*, 1979, 23(6), 347-362.

OCULOSELECTIVE DRUGS AND PRODRUGS

This claims benefit of U.S. Provisional Application No. 60/574,157, filed May 25, 2004, the entire contents of which are incorporated by reference herein.

FIELD OF THE INVENTION

The present invention is directed to compositions useful for the treatment of glaucoma and other conditions. In accordance with preferred embodiments, the compositions of this invention are prodrugs and drugs, the latter comprising beta-blocking agents capable of exerting a localized effect in the eye while substantially avoiding systemic effects.

BACKGROUND OF THE INVENTION

The disclosure of each patent, patent application and publication cited or described in this document is hereby incorporated herein by reference, in its entirety.

Glaucoma is a condition of the eye that is made up of a collection of eye diseases that cause vision loss by damage to the optic nerve. Elevated intraocular pressure (IOP) due to inadequate ocular drainage is a primary cause of glaucoma. Glaucoma can develop as the eye ages, or it can occur as the result of an eye injury, inflammation, tumor, or in advanced cases of cataract or diabetes. It can also be caused by certain drugs, such as steroids. Glaucoma can develop in the absence of elevated IOP. This form of glaucoma has been associated with inheritance (i.e., family history of normal-tension glaucoma) Japanese ancestry, as well as systemic heart disease, such as irregular heartbeat.

There are two main anatomic classifications of glaucoma. These classifications are based on whether the angle of the anterior chamber is open or narrow. The more common open-angle glaucoma is a chronic disease, whereas the less common angle-closure glaucoma is an acute disease. Open-angle glaucoma is usually associated with an increase in intraocular pressure, resulting in damage to the optic nerve and the appearance of cupping of the optic disk. There is an increase in the cup-to-disk ratio and visual dysfunction in the midperipheral field of vision.

Conventional therapy for glaucoma has involved topical administration of pilocarpine and/or epinephrine, and more recently, beta-blockers administered to the eye several times daily. Various beta-blocking agents have been used to lower intraocular pressure. Such use is described, for example, in reviews by W. P. Boger in *Drugs*, 18, 25-32 (1979) and by T. J. Zimmerman and W. P. Boger in *Survey Ophthalmol.* 23(b), 347 (1979). U.S. Pat. No. 4,195,085 to Stone discloses a method for treatment of glaucoma by the ocular administration of a beta-blocking compound, timolol maleate. However, these methods also possess significant drawbacks, in that the absorption of the beta-blocking compound into the systemic circulation can cause undesirable, even life-threatening, side effects. Such side effects result from prolonged beta-blocking action on the heart, bronchioles and blood vessels. Accordingly, there is a need for compounds and a method of treatment of glaucoma or for lowering intraocular pressure that is relatively free of unwanted systemic side effects.

Certain beta-blocking agents that contain enzymatically labile ester groups are known to exhibit short-acting beta-blocking effects in the systemic circulation. Such short-acting beta-blocking compounds (SAABs) have been suggested for treatment or prophylaxis of cardiac disorders as a means for reducing heart work or improving rhythmicity for a short duration. Such short-acting beta-blocking compounds can avoid the sometimes counterproductive effects of conventional beta-blocking agents, whose effects are long-lived and, therefore, difficult to precisely control. Beta-blocking agents having such properties are described in Matier, et al., U.S. Pat. No. 4,402,974, Sep. 6, 1983; Matier, U.S. Pat. Nos. 4,454,154 and 4,455,317.

Topical eye-drops are the most common medical treatment of open-angle glaucoma. Meiotic agents, primarily parasympathetic (e.g., pilocarpine), constrict the pupil to enhance aqueous flow through the trabecular meshwork. The meiotic pupils, however, interfere with night vision. The carbonic anhydrase enzyme inhibitors (e.g., acetazolamide) are orally and topically administered agents (e.g., dorzolamide) that decrease the production of aqueous from the ciliary body, thereby reducing IOP. Recently introduced synthetic prostaglandin analogues (e.g., latanoprost) reduce intraocular pressure by increasing aqueous outflow.

Typically less than 1% of the topically instilled dose is absorbed (N. L. Burstein and J. A. Robinson, J. Ocular Pharmacol. 1, 309 (1985). Even at this low absorption, potent beta-blockers with longer durations of action can cause severe systemic side effects, particularly in patients who also suffer from cardiovascular or bronchoplastic disease. In an attempt to reduce or eliminate such side effects and enhance ocular penetration, several acyl-ester prodrugs of propanolamine-containing beta-blockers have been developed. See, e.g., Vincent, H. L. Lee, and Hans, Bundgaard, "*Prodrugs*", Chapter 7, Marcel Dekker, Inc, Kenneth B. Sloan (ed.), 1992, p. 221; M. Shammem, T. Imai and M. Otagiri, *J. Pharm. Pharmacol.*, 45, 246, 1993 (describing propranolol prodrugs); 246; Hans Bundgaard, Anders Buur, Shih-Chieh Chang and Vincent H. L. Lee, *International Journal of Pharmaceutics*, 77-88, 1988 (describing timolol prodrugs); C G Jordan, *J. Pharm. Sci.*, 87 (7), 880-885, 1998 (describing oxprenolol prodrugs); Patil, et al., U.S. Pat. No. 4,897,417 issued Jan. 30, 1990; and Patil, et al., U.S. Pat. No. 4,966,914 issued Oct. 30, 1990, both discussed in greater detail below.

Among the beta-blocker prodrugs reported in the literature as anti-glaucoma agents, the most common acyl functionality studied is a pivaloyl ester derivative of the secondary hydroxyl group within the oxypropanolamine side chain of the beta-blockers. Interestingly, the physical and chemical characteristics of each pivaloyloxy beta-blocker prodrug are different. For example, the half-life of the oxprenolol prodrug

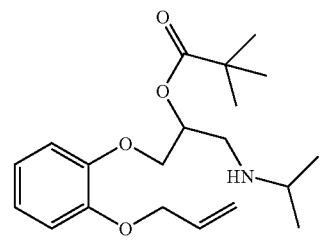

in phosphate buffer (pH 7.4) at 37° C. is 2035.5 days. Under identical conditions, the half-life of the timolol prodrug

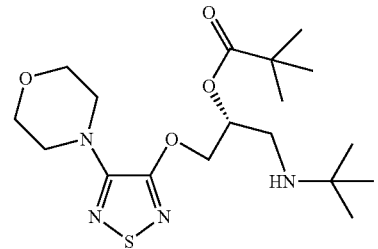

and a compound of Patil, et al., U.S. Pat. No. 4,966,914 of the formula

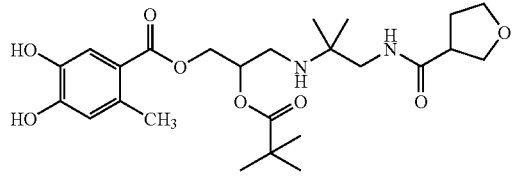

are 3.6 hours and 0.9 hours respectively. These data suggest that the physical and chemical characteristics of an acyl beta-blocker prodrug cannot be predicted solely from the properties of structurally dissimilar yet similarly derivatized beta-blocker prodrugs.

The aforementioned compound disclosed in U.S. Pat. No. 4,966,914 was reported to be an oculoselective beta-blocker having a long duration of action in the ocular fluid and a short duration of action in the systemic circulation. Because of the difference between their intraocular and systemic stabilities, the compound was suggested to provide enhanced intraocular pressure (IOP) reduction capabilities in the eye for extended periods while reducing the level of severe systemic side effects. Two compounds disclosed in U.S. Pat. Nos. 4,897,417 and 4,966,914 to Patil et al.,

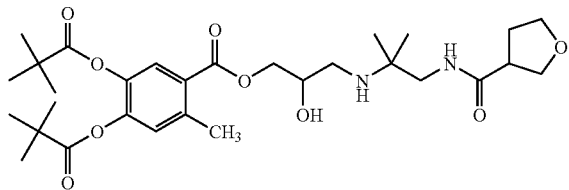

and

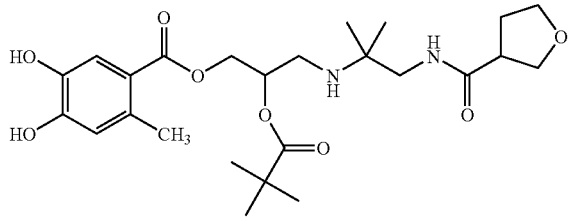

are ester "prodrugs", which are converted in vivo to the active agent of the 914 patent. The prodrugs and their active parent compound were evaluated for their beta-blocking actions, ocular bioavailability and their ocular or systemic safety in animal studies. Neither of the two prodrugs was found sufficient with respect to solution stability and ocular safety profile.

For treatments involving introduction of medicaments into the eye, an ideal beta-blocker prodrug would be stable in buffer solution for good shelf life, and would rapidly hydrolyze in the cornea to deliver the parent compound in the aqueous humor. The parent compound thus provided should be sufficiently stable in the aqueous humor to extend the duration of intraocular pressure lowering, devoid of ocular irritation and local anesthetic activity and rapidly eliminated from systemic circulation to reduce or eliminate systemic effects such as heart failure and bronchospasm. Finally, the prodrug compound should not bind to beta-receptors upon systemic absorption. It can be seen from the foregoing discussion that there is still a need for prodrug forms of beta-blocking agents, as well as novel beta-blocking agents themselves, that possess this combination of desirable features.

SUMMARY OF THE INVENTION

The present invention is directed in part to compounds of Formula I:

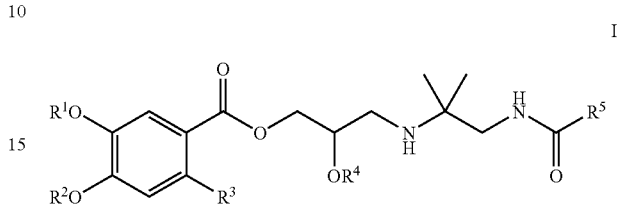

wherein:
$R^1$ and $R^2$ are each independently H, W, or a phenoxyl protecting group;
$R^3$ is hydrogen, straight chain or branched $C_1$-$C_{10}$ alkyl, cycloalkyl, amino, $C_1$-$C_{10}$ alkoxy, —NHC(=O)$R^a$, or —C(=O)N(H)$R^a$;
$R^4$ is H or W, provided that at least one of $R^1$, $R^2$, and $R^4$ is W;
$R^a$ is alkyl, aryl, or heterocyclyl;
$R^5$ is straight chain or branched $C_1$-$C_{10}$ alkyl, cycloalkyl, $C_1$-$C_{10}$ alkoxyalkyl, amino, benzyl, tetrahydrofuranyl, dihydrofuranyl, furanyl, morpholinyl, piperidinyl, tetrahydropyranyl, dioxolanyl, 2,2-dimethyl dioxolanyl, dioxanyl, pyrrolyl, pyrrolidinyl, tetrahydrooxazolyl, dihydrooxazolyl, phenyl, phenyl substituted with $C_1$-$C_{10}$ alkyl, $C_1$-$C_{10}$ alkoxy, or halo, or cycloalkyl substituted with at least one straight or branched $C_1$-$C_{10}$ alkyl;
W is:

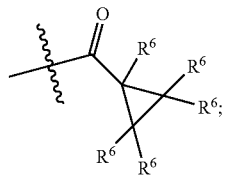

each $R^6$ is independently H, straight chain or branched $C_1$-$C_{10}$ alkyl, or straight chain or branched $C_1$-$C_{10}$ alkoxyalkyl;

or a stereoisomer, hydrate, solvate, acid salt hydrate, or pharmaceutically acceptable salt thereof.

The present invention is also directed in part to compounds of Formula II:

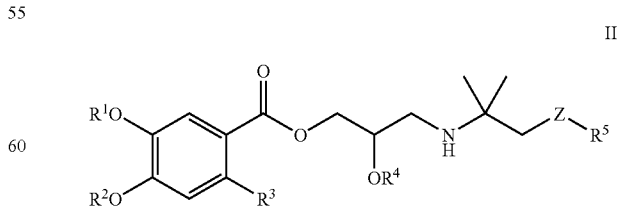

wherein:
$R^1$ and $R^2$ are each independently H, W, or a phenoxyl protecting group;

$R^3$ is hydrogen, straight chain or branched $C_1$-$C_{10}$ alkyl, cycloalkyl, amino, $C_1$-$C_{10}$ alkoxy, —NHC(=O)$R^a$, or —C(=O)N(H)$R^a$;

$R^a$ is alkyl, aryl, or heterocyclyl;

$R^4$ is H or W;

Z is —O— or —O(C=O)—;

$R^5$ is H, straight chain or branched $C_1$-$C_{10}$ alkyl, cycloalkyl, $C_1$-$C_{10}$ alkoxyalkyl, amino, benzyl, tetrahydrofuranyl, dihydrofuranyl, furanyl, morpholinyl, piperidinyl, tetrahydropyranyl, dioxolanyl, 2,2-dimethyl dioxolanyl, dioxanyl, pyrrolyl, pyrrolidinyl, tetrahydrooxazolyl, dihydrooxazolyl, phenyl, phenyl substituted with $C_1$-$C_{10}$ alkyl, $C_1$-$C_{10}$ alkoxy, or halo, or cycloalkyl substituted with at least one straight or branched $C_1$-$C_{10}$ alkyl;

W is:

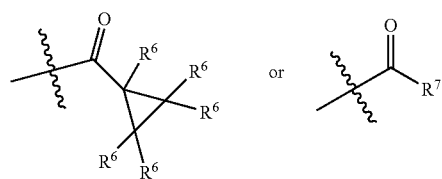

each $R^6$ is independently H, straight chain or branched $C_1$-$C_{10}$ alkyl, or straight chain or branched $C_1$-$C_{10}$ alkoxyalkyl; and $R^7$ is alkyl, cycloalkyl, aryl, or aralkyl;

provided that:

when Z is —O(C=O)—, then $R^5$ is other than H;

or a stereoisomer, hydrate, solvate, acid salt hydrate, or pharmaceutically acceptable salt thereof.

Further, the present invention is directed in part to processes for producing a compound of formula IIIa:

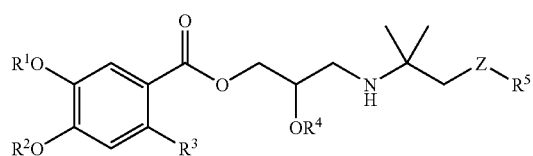

IIIa wherein:

$R^1$ and $R^2$ are each independently H, W, or a phenoxyl protecting group;

$R^3$ is hydrogen, straight chain or branched $C_1$-$C_{10}$ alkyl, cycloalkyl, amino, $C_1$-$C_{10}$ alkoxy, —NHC(=O)$R^a$, or —C(=O)N(H)$R^a$;

$R^4$ is H or W, provided that at least one of $R^1$, $R^2$, and $R^4$ is W;

$R^a$ is alkyl, aryl, or heterocyclyl; and

Z is —O—, —O(C=O)—, or —NH(C=O)—;

$R^5$ is H, straight chain or branched $C_1$-$C_{10}$ alkyl, cycloalkyl, $C_1$-$C_{10}$ alkoxyalkyl, amino, benzyl, tetrahydrofuranyl, dihydrofuranyl, furanyl, morpholinyl, piperidinyl, tetrahydropyranyl, dioxolanyl, 2,2-dimethyl dioxolanyl, dioxanyl, pyrrolyl, pyrrolidinyl, tetrahydrooxazolyl, dihydrooxazolyl, phenyl, phenyl substituted with $C_1$-$C_{10}$ alkyl, $C_1$-$C_{10}$ alkoxy, or halo, or cycloalkyl substituted with at least one straight or branched $C_1$-$C_{10}$ alkyl;

W is:

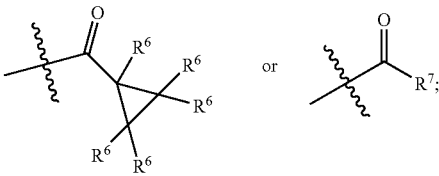

each $R^6$ is independently H, straight chain or branched $C_1$-$C_{10}$ alkyl, or straight chain or branched $C_1$-$C_{10}$ alkoxyalkyl; and $R^7$ is alkyl, cycloalkyl, aryl, or aralkyl;

provided that:

when Z is —O(C=O)—, then $R^5$ is other than H; and when Z is —NH(C=O)—, then $R^5$ is other than H, and W is:

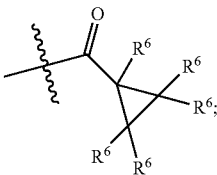

comprising contacting a compound of the formula IIIb.

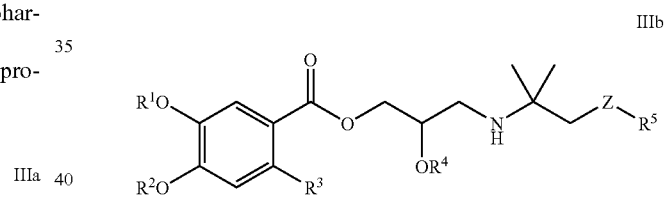

IIIb wherein:

at least one of $R^1$, $R^2$, and $R^4$ is H;

with at least one compound of formula W-L, wherein each L is independently a leaving group;

for a time and under conditions effective to produce a compound of formula IIIa.

In another aspect, the present invention features a pharmaceutical composition for treating a disease or disorder of the eye of a patient, preferably wherein the disease or disorder is glaucoma, intraocular hypertension, or optic neuropathy associated therewith. These compositions comprise an ophthalmologically acceptable carrier or diluent and a compound of Formula I or Formula II as described above.

Also provided in accordance with the present invention are methods of treating diseases or disorders of the eye, namely glaucoma, intraocular hypertension, or the optic neuropathy associated with glaucoma, for example. The methods comprise administering to the eye of the patient a composition comprising an ophthalmologically acceptable carrier or diluent and a compound of Formula I or Formula II in a therapeutically sufficient amount to ameliorate, delay, or prevent the development of, or reduce the symptoms of the disease or disorder.

Other features and advantages of the present invention will be understood by reference to the detailed description and examples that follow.

DETAILED DESCRIPTION OF ILLUSTRATIVE EMBODIMENTS

DEFINITIONS

Figure 1:
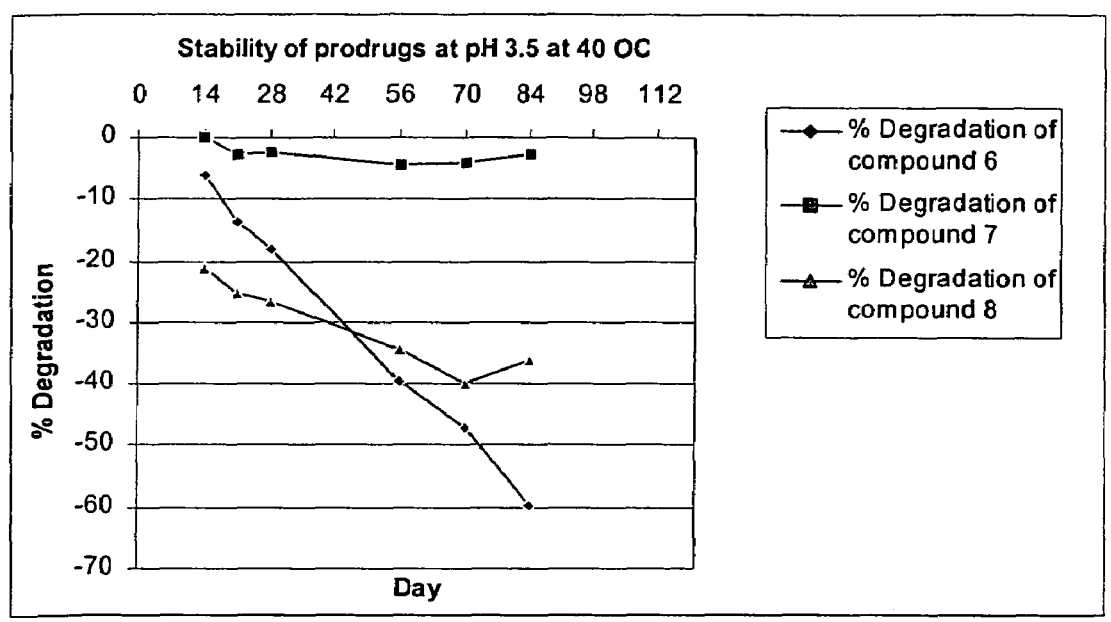
FIG. 1 is a graph showing a time course of the percent degradation of compound 6 (-▲-), compound 7 (-■-) and compound 8 (-♦-) at pH 3.5, 40° C.

As employed above and throughout the disclosure, the following terms, unless otherwise indicated, will be understood to have the following meanings. It will be appreciated that the compounds of the present invention may contain asymmetrically substituted carbon atoms, and may be isolated in optically active or racemic forms. It is well known in the art how to prepare optically active forms, such as by resolution of racemic forms or by synthesis, from optically active starting materials. All chiral, diastereomeric, racemic forms and all geometric isomeric forms of a structure are intended, unless the specific stereochemistry or isomer form is specifically indicated.

"Prodrug" refers to compounds specifically designed to maximize the amount of active species that reaches the desired site of reaction which are of themselves typically inactive or minimally active for the activity desired, but through biotransformation (e.g., enzymatic activity) are converted into biologically active products.

The present invention contemplates the compounds disclosed herein to be used as prodrugs. The term "prodrug" is intended to include compounds of the present invention as well as any molecules that may be transformed into a compound according to Formula (I) or (II) or any other compound of the present invention in vivo following administration to a mammal. A prodrug form of a compound of the present invention can be prepared, for example, by modifying functional groups present in the compound in such a way that the modifications are cleaved, either in routine manipulation or in vivo, to the parent compound. Prodrugs include compounds of the present invention wherein the hydroxy or amino group is bonded to any group that, when the prodrug is administered to a mammal subject, cleaves to form a free hydroxyl or free amino, respectively. Examples of prodrugs include, but are not limited to, acetate, formate and benzoate derivatives of alcohol and amine functional groups in the compounds of the present invention, and the like.

As used herein, the term "side effect" refers to a consequence other than the one(s) for which an agent or measure is used, as the adverse effects produced by a drug, especially on a tissue or organ system other then the one sought to be benefited by its administration. In the case of anti-glaucoma drugs, the term "side effect" may refer to such conditions as, for example, bronchospasm, heart-block or heart failure.

As used herein, the terms "stereoisomer" and "stereoisomers" refer to compounds or mixtures or compounds that have identical chemical constitution, but differ as regards the arrangement of the atoms or groups in space. All chiral, racemic and diastereomeric forms of a structure are intended, except at those chiral centers where the stereochemistry is specifically indicated herein.

"Pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, sorbic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like. These physiologically acceptable salts are prepared by methods known in the art, e.g., by dissolving the free amine bases with an excess of the acid in aqueous alcohol, or neutralizing a free carboxylic acid with an alkali metal base such as a hydroxide, or with an amine.

Compounds described herein throughout, can be used or prepared in alternate forms. For example, many amino-containing compounds can be used or prepared as an acid addition salt. Often such salts improve isolation and handling properties of the compound. For example, depending on the reagents, reaction conditions and the like, compounds as described herein can be used or prepared, for example, as their hydrochloride or tosylate salts. Isomorphic crystalline forms, all chiral and racemic forms, N-oxide, hydrates, solvates, and acid salt hydrates, are also contemplated to be within the scope of the present invention.

Certain compounds of the invention contain amino groups and, therefore, are capable of forming salts with various inorganic and organic acids. Such salts are also within the scope of this invention. Representative salts include acetate, adipate, benzoate, benzenesulfonate, bisulfate, butyrate, citrate, camphorate, camphorsulfonate, ethanesulfonate, fumarate, hemisulfate, heptanoate, hexanoate, hydrochloride, hydrobromide, hydroiodide, methanesulfonate, lactate, maleate, methanesulfonate, 2-naphthalenesulfonate, nitrate, oxalate, pamoate, persulfate, picrate, pivalate, propionate, succinate, sulfate, tartrate, tosylate, and undecanoate. The salts can be formed by conventional means, such as by reacting the free base form of the product with one or more equivalents of the appropriate acid in a solvent or medium in which the salt is insoluble, or in a solvent such as water which is later removed in vacuo or by freeze drying. The salts also can be formed by exchanging the anions of an existing salt for another anion on a suitable ion exchange resin.

Certain acidic or basic compounds of the present invention may exist as zwitterions. All forms of the compounds, including free acid, free base and zwitterions, are contemplated to be within the scope of the present invention. It is well known in the art that compounds containing both amino and carboxyl groups often exist in equilibrium with their zwitterionic forms. Thus, any of the compounds described herein throughout that contain, for example, both amino and carboxyl groups, also include reference to their corresponding zwitterions.

The compounds of the present invention may be used as drugs in connection with pharmaceutically acceptable carriers. The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication commensurate with a reasonable benefit/risk ratio.

The compounds of the present invention can be admixed with carriers, excipients, and/or diluents to form novel compositions. Such compositions can be used in prophylactic, diagnostic, and/or therapeutic techniques. By administering an effective amount of such a composition, prophylactic or therapeutic responses can be produced in a human or some other type mammal. It will be appreciated that the production of prophylactic or therapeutic responses includes the initiation or enhancement of desirable responses, as well as the mitigation, cessation, or suppression of undesirable responses. The compositions of the invention are expected to find many uses, as described in greater detail below.

As used herein, "alkyl" refers to an optionally substituted, saturated straight, branched, or cyclic hydrocarbon having from about 1 to about 20 carbon atoms (and all combinations and subcombinations of ranges and specific numbers of carbon atoms therein), with from about 1 to about 8 carbon atoms, herein referred to as "lower alkyl", being preferred. Alkyl groups include, but are not limited to, methyl, ethyl, n-propyl, isopropyl, n-butyl, isobutyl, t-butyl, n-pentyl, cyclopentyl, isopentyl, neopentyl, n-hexyl, isohexyl, cyclohexyl, cyclooctyl, adamantyl, 3-methylpentyl, 2,2-dimethylbutyl, and 2,3-dimethylbutyl.

As used herein, "halo" and "halogen" each refers to a fluoro, chloro, bromo, or iodo moiety attached to a compound of the invention. Preferably, "halo" and "halogen" refer to fluoro or chloro moieties.

As used herein, "heteroaryl" refers to an optionally substituted, mono-, di-, tri-, or other multicyclic aromatic ring system that includes at least one, and preferably from 1 to about 4 sulfur, oxygen, or nitrogen heteroatom ring members. Heteroaryl groups can have, for example, from about 3 to about 50 carbon atoms (and all combinations and subcombinations of ranges and specific numbers of carbon atoms therein), with from about 4 to about 10 carbons being preferred. Non-limiting examples of heteroaryl groups include, for example, pyrryl, furyl, pyridyl, 1,2,4-thiadiazolyl, pyrimidyl, thienyl, isothiazolyl, imidazolyl, tetrazolyl, pyrazinyl, pyrimidyl, quinolyl, isoquinolyl, thiophenyl, benzothienyl, isobenzofuryl, pyrazolyl, indolyl, purinyl, carbazolyl, benzimidazolyl, and isoxazolyl. The term "heteroaryl ring carbon" refers to a carbon atom located within the ring framework, wherein heteroaryl is as defined above.

As used herein, the terms "alkoxy" and "alkoxyl" refer to an optionally substituted alkyl-O— group wherein alkyl is as previously defined. Exemplary alkoxy and alkoxyl groups include methoxy, ethoxy, n-propoxy, i-propoxy, n-butoxy, and heptoxy.

"Haloalkoxyl" or "Haloalkoxy" is intended to include both branched and straight-chain saturated aliphatic hydrocarbon groups having the specified number of carbon atoms, substituted with 1 or more halogen. The use of the prefixes "mono- and poly- refer to substitution by one or by two or more, respectively. Examples of haloalkyl groups include, but are not limited to, trifluoromethyl, trichloromethyl, pentafluoroethyl, and pentachloroethyl groups.

As used herein, the term "spiroalkyl" refers to an alkylene diradical, both ends of which are bonded to the same carbon atom of the parent group to form a spirocyclic group. The spiro alkyl group, taken together with its parent group, as herein defined, has 3 to 20 ring atoms. Preferably, it has 3 to 10 ring atoms. Non-limiting examples of a spiroalkyl group taken together with its parent group include 1-(1-methyl-cyclopropyl)-propan-2-one, 2-(1-phenoxy-cyclopropyl)-ethylamine, and 1-methyl-spiro[4.7]dodecane. The spiroalkyl groups of this invention can be substituted or unsubstituted.

Alkenyl and alkynyl groups include both straight and branched carbon chains. Alkenyl groups according to the invention are straight chain or branched chain alkyl moieties that include one or more carbon-carbon double bonds. Preferred alkenyl groups are those having two to about ten carbon atoms. Alkynyl groups according to the invention are straight or branched chain alkyl moieties that include one or more carbon-carbon triple bonds. Thus, alkenyl and alkynyl groups according to the invention include, but are not limited to, hydrocarbons such as ethene, ethyne, propene, propyne, butenyl, pentynyl, 2-butenyl, 2-methylbutynyl, and isopentenyl moieties having 1 to about 10 carbon atoms, and in some aspects of the invention, preferably 1 to about 6 carbon atoms.

As used herein, "aralkyl" refers to alkyl radicals bearing an aryl substituent and have from about 6 to about 50 carbon atoms (and all combinations and subcombinations of ranges and specific numbers of carbon atoms therein), with from about 6 to about 10 carbon atoms being preferred. Aralkyl groups can be optionally substituted. Non-limiting examples include, for example, benzyl, diphenylmethyl, triphenylmethyl, phenylethyl, and diphenylethyl.

As used herein, "aryl" refers to an optionally substituted, mono-, di-, tri-, or other multicyclic aromatic ring system having from about 5 to about 50 carbon atoms (and all combinations and subcombinations of ranges and specific numbers of carbon atoms therein), with from about 6 to about 10 carbons being preferred. Non-limiting examples include, for example, phenyl, naphthyl, anthracenyl, and phenanthrenyl.

As used herein, "heterocyclyl" refers to a mono-, di-, tri-, or other multicyclic aliphatic ring system that includes at least one, and preferably from 1 to about 4 sulfur, oxygen, or nitrogen heteroatom ring members. Heterocyclyl groups can have from about 3 to about 20 carbon atoms (and all combinations and subcombinations of ranges and specific numbers of carbon atoms therein), with from about 4 to about 10 carbons being preferred. The heterocyclyl group may be unsaturated, and may also be fused to aromatic rings. Examples of heterocyclyl groups include, for example, tetrahydrofuranyl, tetrahydrothienyl, piperidinyl, pyrrolidinyl, isoxazolidinyl, isothiazolidinyl, pyrazolidinyl, oxazolidinyl, thiazolidinyl, piperazinyl, morpholinyl, piperidinyl, decahydroquinolyl, octahydrochromenyl, octahydro-cyclopenta[c]pyranyl, 1, 2, 3, 4,-tetrahydroquinolyl, octahydro-[2]pteridinyl, decahydro-cycloocta[c]furanyl, and imidazolidinyl. Heterocyclyl groups can be substituted or unsubstituted.

The compounds and intermediates of the present invention may contain protecting groups. Protecting groups are known per se as chemical functional groups that can be selectively appended to and removed from functionality, such as hydroxyl and amine groups, present in a chemical compound to render such functionality inert to certain chemical reaction conditions to which the compound is exposed. See, e.g., Greene and Wuts, *Protective Groups in Organic Synthesis,* 2d edition, John Wiley & Sons, New York, 1991. Numerous hydroxyl protecting groups are known in the art, including the acid-labile t-butyldimethylsilyl, diethylisopropylsilyl, and triethylsilyl groups and the acid-stable aralkyl (e.g., benzyl), triisopropylsilyl, and t-butyldiphenylsilyl groups. Useful amine protecting groups include the allyloxycarbonyl (Alloc), benzyloxycarbonyl (CBz), chlorobenzyloxycarbonyl, t-butyloxycarbonyl (Boc), fluorenylmethoxycarbonyl (Fmoc), isonicotinyloxycarbonyl (I-Noc) groups.

As used herein, "phenoxyl protecting groups" refer to chemical functional groups that can be selectively appended to and removed from the hydroxyl functionality present in phenolic compound (Ar—OH) to render such functionality inert to certain chemical reaction conditions to which the compound is exposed. In compounds of the invention where two phenoxyl groups are present, each may bear its own independent protecting group. Alternatively, one dual function protecting group may be employed to protect both phenoxyl groups simultaneously, such that the two phenoxyl groups together with the carbon atoms through which they are connected form a dioxanyl (six-membered ring wherein two oxygen atoms are placed at ring positions 1 and 3 relative to each other) or dioxolanyl (five-membered ring wherein two oxygen atoms are placed at ring positions 1 and 3 relative to each other) ring. Examples of phenoxyl protecting groups include benzyl and substituted aralkyl. Examples of dual function protecting groups include the acetal or ketal moiety from the adjacent phenoxyl groups with an aldehyde or ketone respectively. Additional examples of phenoxyl and catechol (two adjacent phenoxyl groups) protecting groups may be found in Greene and Wuts, *Protective Groups in Organic Synthesis,* 2d edition, John Wiley & Sons, New York, 1991.

As used herein, "alkoxyalkyl" refers to an alkyl group wherein one or more of the hydrogen atoms on the alkyl is replaced by an alkoxy moiety. Alkoxyalkyl groups can have from about 2 to about 20 carbon atoms (and all combinations and subcombinations of ranges and specific numbers of carbon atoms therein), with from about 2 to about 10 carbons being preferred. Examples of alkoxyalkyl group include, for example, ethoxymethyl, methoxymethyl, methoxy butyl, methoxy ethyl and propoxymethyl. Alkoxyalkyl groups can be substituted or unsubstituted. Lower alkoxyalkyl moieties can have from about 2 to about 10 carbons atoms. More preferably, they have from about 2 to about 6 carbon atoms.

As used herein, "cycloalkyl" refers to an optionally substituted, alkyl group having one or more rings in their structures having from about 3 to about 20 carbon atoms (and all combinations and subcombinations of ranges and specific numbers of carbon atoms therein), with from about 3 to about 10 carbon atoms being preferred. Multi-ring structures may be bridged or fused ring structures groups include, but are not limited to, cyclopropyl, cyclobutyl, cyclopentyl, cyclohexyl, cyclooctyl, 2-[4-isopropyl-1-methyl-7-oxa-bicyclo[2.2.1] heptanyl], 2-[1,2,3,4-tetrahydro-naphthalenyl], and adamantyl.

As used herein, the terms "aralkoxy" and "aralkoxyl" refer to an optionally substituted aralkyl-O— group wherein aralkyl is as previously defined. Exemplary aralkoxy and aralkoxyl groups include benzyloxy, 1-phenylethoxy, 2-phenylethoxy, and 3-naphthylheptoxy.

As used herein, the term aralkoxyalkyl refers to an optionally substituted aralkyl-O-alkyl-group wherein aralkoxyl and alkyl are as previously defined. Exemplary aralkoxyalkyl groups include benzyloxymethyl, 2,4-dimethylbenzyloxymethyl, 3-trifluoromethylbenzyloxymethyl, naphthylethyloxypropyl and 3-(phenethyloxy)-2-methylpropyl.

It will be appreciated that groups according to the invention can be unsubstituted or can bear one or more substituents. For example, in some embodiments, the terms "cyclohexyl", "benzyl", "furanyl", "tetrahydrofuranyl", "dihydrofuranyl", "morpholinyl", "piperidinyl", "tetrahydropyranyl", "dioxolanyl", "dioxanyl", "pyrrolinyl", "tetrahydrooxazolyl" and "dihydrooxazolyl" refer to the involved moieties as being optionally substituted. Typically, substituted chemical moieties include one or more substituents that replace hydrogen. Thus, "Substituted" is intended to indicate that one or more hydrogens of the identified moiety is replaced with a selection from the indicated group(s), provided that the normal valency in the identified moiety is not exceeded, and that the substitution results in a stable compound. Exemplary substituents include, for example, halo (e.g., —F, —Cl, —Br), provided that when halo is —Br, said —Br is attached to an aryl or heteroaryl ring carbon, alkoxy, monohaloalkoxy, polyhaloalkoxy, alkyl, spiroalkyl, alkenyl, alkynyl, aralkyl, aryl, heteroaryl, heterocyclyl, hydroxyl (—OH), nitro (—NO$_2$), cyano (—CN), sulfonyl (—SO$_2$R'), sulfamoyl (—SO$_2$NR"R'''), amino (—NH$_2$, NHR", NHR''', N(R"R''')) and the like, wherein each R', R" and R''' may independently include alkyl, aryl, aralkyl cycloalkyl, cycloalkylalkyl, heterocycloalkyl, heteroaryl and the like. When a substituent is =O (a keto group), then two hydrogens on the implicated carbon atom are replaced. By way of illustration, when a carbon ring containing one oxygen is substituted on the carbon adjacent to the oxygen =O, a lactone is formed.

When any variable occurs more than one time in any constituent or in any formula, its definition in each occurrence is independent of its definition at every other occurrence. Thus, for example, if a W group is shown to be substituted with, for example, 1 to 5 of straight chain or branched $C_1$-$C_{10}$ alkyl, or straight chain or branched $C_1$-$C_{10}$ alkoxyalkyl, then said W group may optionally be substituted with up to five of the above mentioned substituents, and the substituent at each occurrence is selected independently from the above defined list of possible substituents. Combinations of substituents and/or variables are permissible only if such combinations result in stable compounds. It is further understood that, while certain substituents are minimally required, such as, for example in the W moiety, the moiety may be further substituted with the same substituent(s), another substituent(s) from the group of required substituents, or other substituent(s) not from the group of required substituents.

"Stable compound" and "stable structure" are meant to indicate a compound that is sufficiently robust to survive isolation to a useful degree of purity from a reaction mixture, and formulation into an efficacious therapeutic agent. Stable compounds are preferred in accordance with the present invention.

It is believed the chemical formulas and names used herein correctly and accurately reflect the underlying chemical compounds. However, the nature and value of the present invention does not depend upon the theoretical correctness of these formulae, in whole or in part. Thus it is understood that the formulas used herein, as well as the chemical names attributed to the correspondingly indicated compounds, are not intended to limit the invention in any way, including restricting it to any specific tautomeric form or to any specific optical; or geometric isomer, except where such stereochemistry is clearly defined.

As used herein, the term "contacting" refers to the bringing together of compounds to within distances that allow for intermolecular interactions and chemical transformations accompanying such interactions. Often, contacting compounds are in solution phase.

"Subject" or "patient" refers to animals, including mammals, preferably humans.

"Effective amount" refers to an amount of a compound as described herein that may be therapeutically effective to inhibit, prevent or treat the symptoms of particular disease, disorder, condition, or side effect.

Description:

Compounds. One aspect of the present invention features ester group-containing compounds that have a selective, localized, beta-blocking effect in the eye after topical administration. While not wanting to be bound by theory, such compounds are thought to be rapidly inactivated by metabolism upon entering the systemic circulation and, therefore, may not be available to act at the receptor in the heart and the lungs. It has been discovered that these same compounds are relatively stable in ocular fluids, i.e., lacrimal fluids and aqueous humor, and ocular tissue such as the iris-ciliary complex. Consequently, such compounds are useful for the treatment of glaucoma or for lowering intraocular pressure since they remain stable when topically applied to the eye but rapidly metabolize when subsequently absorbed into the systemic circulation. Thus, the compounds and methods of the present invention provide a very useful therapeutic alternative for the treatment of glaucoma or for lowering intraocular pressure, among other advantageous features.

Compounds of the present invention comprise Formula I or Formula II as described herein. Formulas I and II include novel classes of prodrugs that undergo hydrolysis upon corneal penetration to form potent beta-adrenergic blocking agents that have a long half-life in the aqueous humor. In addition, the prodrugs have one or more features that renders them distinctly advantageous for ophthalmic use. For instance, compounds of the invention have been shown to be stable in buffer solution for good shelf life, and to rapidly hydrolyze in the cornea to deliver the active compound in the aqueous humor. The active compounds thus provided are sufficiently stable in the aqueous humor to extend the duration of their effectiveness in lowering intraocular pressure as compared to known compounds. In some embodiments, the compounds of the invention have reduced ocular irritation or local anesthetic activity. In some preferred embodiments, the compounds are substantially devoid of ocular irritation or local anesthetic activity. Even more preferably, they are substantially devoid of ocular irritation and local anesthetic activity. In some preferred embodiments, active compounds are rapidly eliminated from systemic circulation to reduce or eliminate systemic effects such as heart failure and bronchospasm. In some embodiments the prodrug compound does not appreciably bind to beta-receptors upon systemic absorption. By prodrug compound, it is meant that at least one of $R^1$, $R^2$, and $R^4$ is W. In some preferable embodiments $R^4$ is H; more preferably when $R^4$ is H, at least one of $R^1$ and $R^2$ is also H. In certain preferred embodiments $R^1$, $R^2$, and $R^4$ are each H.

Hydrolysis of Formula I compounds results in the formation of beta-blocking compounds such as those described in Patil, et al., U.S. Pat. No. 4,966,914. Notably, though, in accordance with the present invention, the beta-blocking drugs formed by hydrolysis of Formula II compounds constitute a new class of beta-blockers that heretofore have not been described. Thus, Formula II includes both prodrugs and drugs. The prodrugs have the features and advantages described above. The drugs encompassed by Formula II will have utility not only for treatment of glaucoma, but also for a wide variety of other purposes for which short-acting beta-blockers are known to be suitable or preferred. For example, catechol-containing beta-blocking compounds such as those described in U.S. Pat. No. 4,966,914 and encompassed by Formula II have been shown to exert a potent antioxidant and myocardial cytoprotective efficacy against free radical-mediated cardiac membrane lipid peroxidation (Mousa, et al., 1992, *Int. J. Clin. Pharmacol. Therap. Toxicol.* 30: 103-106), thereby augmenting their utility for treatment of post-traumatic or post-operative conditions of the heart, among other cardiovascular utilities. Furthermore, inasmuch as lipid peroxidation inhibitors have been demonstrated to exert a neuroprotective effect (Huh, et al., 2000, *Eur. J. Pharmacol.* 389: 79-88), the beta-blocking drugs encompassed by Formula II should find utility for treatment of a variety acute and chronic neurological conditions in which neuroprotection imparts a benefit. Such conditions include, but are not limited to: acute neurodegenerative disorders such as ischemia from stroke or associated with focal or diffuse brain trauma, diffuse brain damage and spinal cord injury, as well as chronic conditions or diseases such as Alzheimer's disease, dementia, Parkinson's disease, amyotrophic lateral sclerosis, multiple sclerosis, cerebral palsy, and the optic neuropathy associated with glaucoma. Other indications for which the compounds of the invention may be used to advantage include, but are not limited to, treatment of high blood pressure, control of angina, treatment of certain abnormal heart rhythms, prolonging survival of patients who have had a heart attack, treatment of hypertrophic cardiomyopathy, treatment of heart failure, treatment of vasovagal fainting, treatment of migraines, treatment of essential tremor, prevention of bleeding from esophageal varices and prevention or reduction of stage fright.

In certain embodiments of compounds of the invention, $R^1$ and $R^2$ are each independently H, W, or a phenoxyl protecting group. In some preferred embodiments $R^1$ and $R^2$ are each independently H or W, or $R^1$ and $R^2$ may each independently be a phenoxyl protecting group. In certain of the embodiments where $R^1$ and $R^2$ are each independently a phenoxyl protecting group, one moiety may act as a protecting group incorporating $R^1$ and $R^2$ and the atoms through which they are connected into dioxane or dioxolane ring. In other preferable embodiments, at least one of $R^1$ and $R^2$ is H; more preferably both $R^1$ and $R^2$ are H. Preferably when both $R^1$ and $R^2$ are H, at least one of the $R^6$ substituents is independently other than H. In some embodiments, the hydroxyl protecting group is a cyclic ketal or acetal formed by reaction of the catechol derivative (compound wherein $R^1$ and $R^2$ are both H with a ketone or aldehyde respectively). In some embodiments, $R^1$ and $R^2$ are each independently aralkyl, preferably benzyl.

In other embodiments, $R^4$ is H or W. In certain preferred embodiments at least one of $R^1$, $R^2$, and $R^4$ is W; more preferably $R^4$ is W. Yet more preferably when $R^4$ is W, both $R^1$ and $R^2$ are H. Preferably when $R^4$ is W, at least one of the $R^6$ substituents is independently other than H. More preferably when $R^4$ is W and both $R^1$ and $R^2$ are H, at least one of the $R^6$ substituents is independently other than H.

In yet other embodiments where $R^1$ and $R^2$ are each independently H, W, or a phenoxyl protecting group, and $R^4$ is H or W, at least one of $R^1$, $R^2$, and $R^4$ is W.

In some embodiments, $R^3$ is hydrogen, straight chain or branched $C_1$-$C_{10}$ alkyl, cycloalkyl, amino, $C_1$-$C_{10}$ alkoxy, —NHC(=O)$R^a$, or —C(=O)N(H)$R^a$, wherein $R^a$ is alkyl, aryl, or heterocyclyl; preferably $R^3$ is H or straight chain or branched $C_1$-$C_{10}$ alkyl, more preferably H or straight chain or branched $C_1$-$C_5$ alkyl, more preferably still, H or methyl, yet more preferably methyl.

In some other embodiments, Z is —O—, —O(C=O)—, or —NH(C=O)—. In certain embodiments Z is —NH(C=O)—. In other embodiments, Z is —O(C=O)— or —O—. In yet other embodiments, Z is —O(C=O)—. In still other embodiments, Z is —O—.

In some embodiments, $R^5$ is H, straight chain or branched $C_1$-$C_{10}$ alkyl, cycloalkyl, $C_1$-$C_{10}$ alkoxyalkyl, amino, benzyl, tetrahydrofuranyl, dihydrofuranyl, furanyl, morpholinyl, piperidinyl, tetrahydropyranyl, dioxolanyl, 2,2-dimethyl dioxolanyl, dioxanyl, pyrrolyl, pyrrolidinyl, tetrahydrooxazolyl, dihydrooxazolyl, phenyl, phenyl substituted with $C_1$-$C_{10}$ alkyl, $C_1$-$C_{10}$ alkoxy, or halo, or cycloalkyl substituted with at least one straight or branched $C_1$-$C_{10}$ alkyl.

In other embodiments, $R^5$ is straight chain or branched $C_1$-$C_{10}$ alkyl, cycloalkyl, $C_1$-$C_{10}$ alkoxyalkyl, amino, benzyl, tetrahydrofuranyl, dihydrofuranyl, furanyl, morpholinyl, piperidinyl, tetrahydropyranyl, dioxolanyl, 2,2-dimethyl dioxolanyl, dioxanyl, pyrrolyl, pyrrolidinyl, tetrahydrooxazolyl, dihydrooxazolyl, phenyl, phenyl substituted with $C_1$-$C_{10}$ alkyl, $C_1$-$C_{10}$ alkoxy, or halo, or cycloalkyl substituted with at least one straight or branched $C_1$-$C_{10}$ alkyl.

In some other embodiments $R^5$ is straight chain or branched $C_1$-$C_{10}$ alkyl, amino, cyclohexyl, benzyl, tetrahydrofuranyl, dihydrofuranyl, furanyl, phenyl or phenyl substituted with $C_1$-$C_{10}$ alkyl, $C_1$-$C_{10}$ alkoxy, or halo. In some embodiments, cyclohexyl, benzyl, tetrahydrofuranyl, dihydrofuranyl, and furanyl are optionally substituted.

In other embodiments $R^5$ is H, straight chain or branched $C_1$-$C_{10}$ alkyl, cycloalkyl, $C_1$-$C_{10}$ alkoxyalkyl, phenyl, phenyl substituted with $C_1$-$C_{10}$ alkyl, $C_1$-$C_{10}$ alkoxy, or halo, or cycloalkyl substituted with at least one straight or branched $C_1$-$C_{10}$ alkyl.

In some embodiments $R^5$ is straight chain or branched $C_1$-$C_{10}$ alkyl, alkoxyalkyl, amino, cyclohexyl, benzyl, tetrahydrofuranyl, phenyl, or phenyl substituted with $C_1$-$C_{10}$ alkyl, $C_1$-$C_{10}$ alkoxy, or halo. In some embodiments, cyclohexyl, benzyl, tetrahydrofuranyl, dihydrofuranyl and furanyl are optionally substituted. More preferably, they are substituted with alkyl.

In yet other embodiments, $R^5$ is straight chain or branched $C_1$-$C_{10}$ alkyl, amino, cyclohexyl, benzyl, tetrahydrofuranyl, dihydrofuranyl, furanyl, morpholinyl, piperidinyl, tetrahydropyranyl, dioxolanyl, dioxanyl, pyrrolinyl, tetrahydrooxazolyl or dihydrooxazolyl, or phenyl or phenyl substituted with $C_1$-$C_{10}$ alkyl, $C_1$-$C_{10}$ alkoxy, or halo. In some embodiments, cyclohexyl, benzyl, tetrahydrofuranyl, dihydrofuranyl, furanyl, morpholinyl, piperidinyl, tetrahydropyranyl, dioxolanyl, dioxanyl, pyrrolinyl, tetrahydrooxazolyl, or dihydrooxazolyl are optionally substituted. More preferably, they are substituted with alkyl.

In some preferred embodiments, $R^5$ is furanyl, dihydrofuranyl, or tetrahydrofuranyl. More preferably, $R^5$ is tetrahydrofuran-2-yl or tetrahydrofuran-3-yl. Even more preferably $R^5$ is tetrahydrofuran-3-yl. In some alternative preferable embodiments, tetrahydrofuran-3-yl is optionally substituted. More preferably, the tetrahydrofuran-3-yl is substituted with at least one alkyl.

In other embodiments, when Z is —NH(C═O)—, $R^5$ is straight chain or branched $C_1$-$C_{10}$ alkyl, amino, cyclohexyl, benzyl, tetrahydrofuranyl, dihydrofuranyl, furanyl, phenyl, or phenyl substituted with $C_1$-$C_{10}$ alkyl, $C_1$-$C_{10}$ alkoxy, or halo.

In other embodiments, when Z is —NH(C═O)—, $R^5$ is straight chain or branched $C_1$-$C_{10}$ alkyl, amino, cyclohexyl, benzyl, tetrahydrofuranyl, dihydrofuranyl, furanyl, morpholinyl, piperidinyl, tetrahydropyranyl, dioxolanyl, , dioxanyl, pyrrolinyl, tetrahydrooxazolyl or dihydrooxazolyl, or phenyl or phenyl substituted with $C_1$-$C_{10}$ alkyl, $C_1$-$C_{10}$ alkoxy, or halo.

In certain embodiments, $R^5$ is straight chain or branched $C_1$-$C_{10}$ alkyl, amino, cyclohexyl, benzyl, tetrahydrofuranyl, dihydrofuranyl, furanyl, morpholinyl, piperidinyl, tetrahydropyranyl, dioxolanyl, dioxanyl, pyrrolinyl, tetrahydrooxazolyl, dihydrooxazolyl, phenyl, or phenyl substituted with $C_1$-$C_{10}$ alkyl, $C_1$-$C_{10}$ alkoxy, or halo; and W is:

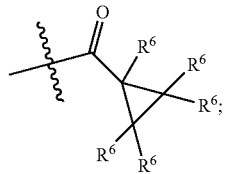

wherein each $R^6$ is independently H, straight chain or branched $C_1$-$C_{10}$ alkyl, or straight chain or branched $C_1$-$C_{10}$ alkoxyalkyl. In some preferred embodiments, at least one of $R^6$ is other than H. In other preferred embodiments, at least one of $R^6$ is $C_1$-$C_5$ alkyl, more preferably $C_1$-$C_3$ alkyl, even more preferably methyl. In certain other preferred embodiments, at least one of $R^6$ is alkoxypropyl, alkoxyethyl, or alkoxymethyl; more preferably wherein said alkoxy of said alkoxypropyl, alkoxyethyl, or alkoxymethyl is $C_1$-$C_5$ alkoxy, even more preferably $C_1$-$C_3$ alkoxy, yet more preferably methoxy.

In some preferred embodiments, $R^5$ is furanyl, dihydrofuranyl, or tetrahydrofuranyl. More preferably, $R^5$ is tetrahydrofuran-2-yl or tetrahydrofuran-3-yl. Even more preferably $R^5$ is tetrahydrofuran-3-yl. Yet more preferably, when $R^5$ is tetrahydrofuran-3-yl it is substituted with alkyl.

In some embodiments, $R^5$ is alkyl substituted tetrahydrofuranyl. Preferably, it is 3-alkyltetrahydrofuranyl. Even more preferably, $R^5$ is 3-alkyltetrahydrofuran-3-yl.

In certain embodiments when Z is —O—, $R^5$ is H, straight chain or branched $C_1$-$C_{10}$ alkyl, cycloalkyl, $C_1$-$C_{10}$ alkoxyalkyl, phenyl, phenyl substituted with $C_1$-$C_{10}$ alkyl, $C_1$-$C_{10}$ alkoxy, or halo, or cycloalkyl substituted with at least one straight or branched $C_1$-$C_{10}$ alkyl.

In certain embodiments when Z is —O—, $R^5$ is H, straight chain or branched $C_1$-$C_{10}$ alkyl, cycloalkyl, cycloalkyl substituted with at least one straight or branched $C_1$-$C_{10}$ alkyl, $C_1$-$C_{10}$ alkoxyalkyl, amino, benzyl, tetrahydrofuranyl, dihydrofiranyl, furanyl, morpholinyl, piperidinyl, tetrahydropyranyl, dioxolanyl, 2,2-dimethyl dioxolanyl, dioxanyl, pyrrolyl, pyrrolidinyl, tetrahydrooxazolyl, dihydrooxazolyl, phenyl, or phenyl substituted with $C_1$-$C_{10}$ alkyl, $C_1$-$C_{10}$ alkoxy, or halo.

In certain embodiments when Z is —O(C═O)—, is straight chain or branched $C_1$-$C_{10}$ alkyl, alkoxyalkyl, amino, cyclohexyl, tetrahydrofuranyl, 3-alkyl tetrahydrofuranyl, benzyl, phenyl, or phenyl substituted with $C_1$-$C_{10}$ alkyl, $C_1$-$C_{10}$ alkoxy, or halo.

In certain other embodiments when Z is —O(C═O)—, $R^5$ is straight chain or branched $C_1$-$C_{10}$ alkyl, alkoxyalkyl, amino, cyclohexyl, benzyl, tetrahydrofuranyl, phenyl or phenyl substituted with $C_1$-$C_{10}$ alkyl, $C_1$-$C_{10}$ alkoxy, or halo.

In still other embodiments W is:

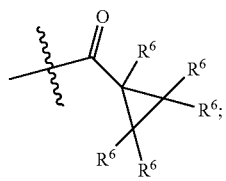

wherein each $R^6$ is independently H, straight chain or branched $C_1$-$C_{10}$ alkyl, or straight chain or branched $C_1$-$C_{10}$ alkoxyalkyl; or W may be —C(=O)—R⁷, wherein R⁷ is alkyl, cycloalkyl, aryl, or aralkyl. Preferably when W is:

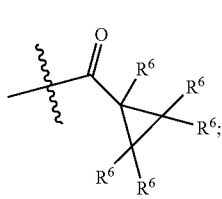

at least one of the R⁶ substituents is independently other than H. Preferably each R⁶ is independently H, $C_1$-$C_5$ alkyl, or lower alkoxyalkyl, more preferably independently H or $C_1$-$C_5$ alkyl. Alternatively, each R⁶ independently may be H, methyl or $CH_2OCH_3$, more preferably independently H or methyl. Alternatively, each R⁶ independently may be H or $CH_2OCH_3$.

In still other preferable embodiments, each W is independently:

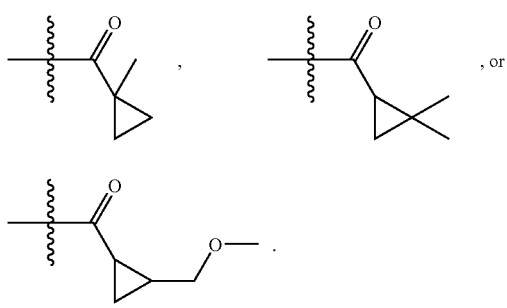

More preferably, when R¹ and R² are H, R⁴ is:

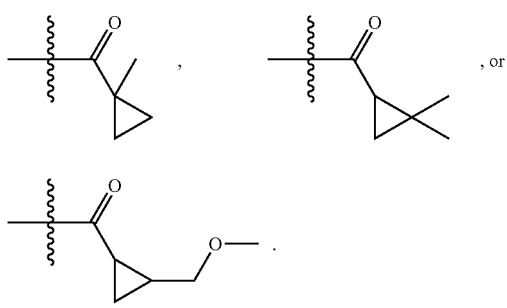

In certain preferable embodiments, the compounds of Formula I have the following structure:

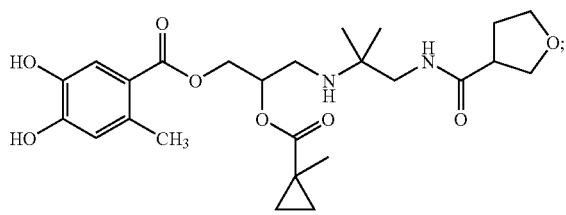

more preferably,

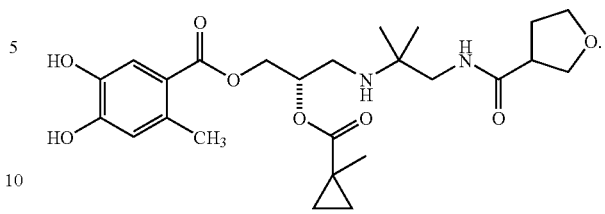

In certain preferable embodiments, the compounds of Formula I or II have the following stereochemistry:

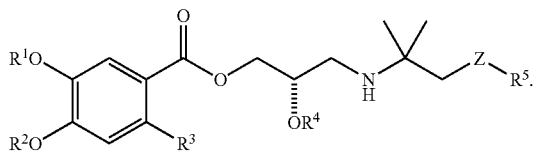

In certain embodiments, the present invention is related to compounds of Formula I or II, or stereoisomers, pharmaceutically acceptable salts, hydrates, solvates, acid salt hydrates or isomorphic crystalline forms thereof. In certain preferred embodiments, the compounds are provided as pharmaceutical salts of formula:

[A].HX;

wherein A is a compound of formula I or II and HX is an acid. In embodiments wherein A is a compound of formula I or II it preferably has the structure:

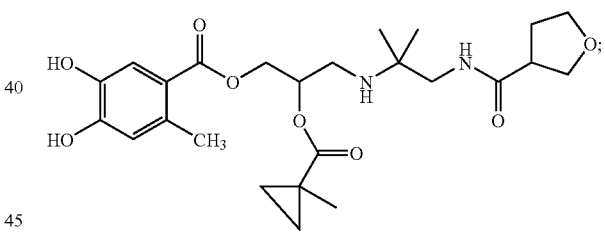

yet more preferably A is a compound having the structure:

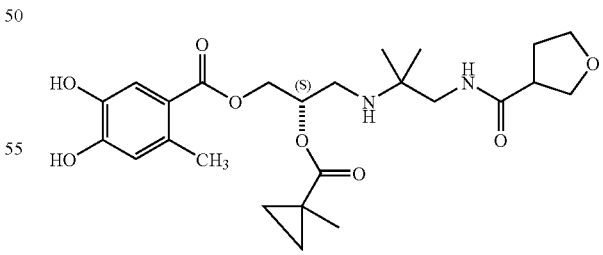

and HX is an acid; more preferably, the acid is selected from the group consisting of hydrochloric, sulfuric, maleic, fumaric, oxalic, succinic, citric, and tartaric acids. In other preferred embodiments, the compounds are provided as pharmaceutical salts of formula:

[A].HX;

wherein A is a compound of formula I or II and HX is an acid; more preferably, the acid is selected from the group consisting of hydrochloric, sulfuric, maleic, fumaric, oxalic, succinic, citric, and tartaric acids.

Compounds of the invention and equivalents thereof possessing substantially similar pharmacological properties may be prepared in accordance with standard synthetic chemistry protocols. Several such protocols are set forth in the examples herein. A general scheme is provided outlining a typical procedure for the preparation of compounds of the invention (Scheme 1). Benzoic acid I may be reacted with a racemic or chiral activated epoxy propane derivative II to provide the glycidyl ester III. Reactions may be carried out in the presence or absence of solvent over a wide range of conditions, for example using a base such as sodium hydride in N-methyl pyrrolidinone at 0-25° C. The optional use of a chiral glycidyl derivative II allows the introduction of chirality into the final compound, if desired. Ester III may be further reacted with IV with or without added base to form the secondary alcohol V. Typical solvents include N-methyl pyrrolidinone and acetonitrile. The choice of base is not usually important so long as it does not substantially interfere with the reaction. For example, an amine base such as triethylamine may be added. Compounds of structure V or VI may be further derivatized if required. For example, when Z-$R^5$ is —OH, V may be further esterified or etherified by known methods as for example in Wuts, to provide the corresponding ester or ether. Alternatively, the diamine or aminoalcohol corresponding to IV may be esterified, etherified or N-acylated prior to reaction with compound III. Compound V (in racemic or chiral form) may be further esterified with $R^4$-L using general esterification procedures (where L is an appropriate leaving group), such as those in Greene, T. W. and Wuts, P. G. M., *Protective Groups in Organic Synthesis* 2d. Ed., Wiley & Sons, 1991, disclosure of which is hereby incorporated herein by reference, in its entirety, to yield VI (one stereoisomer shown as an example).

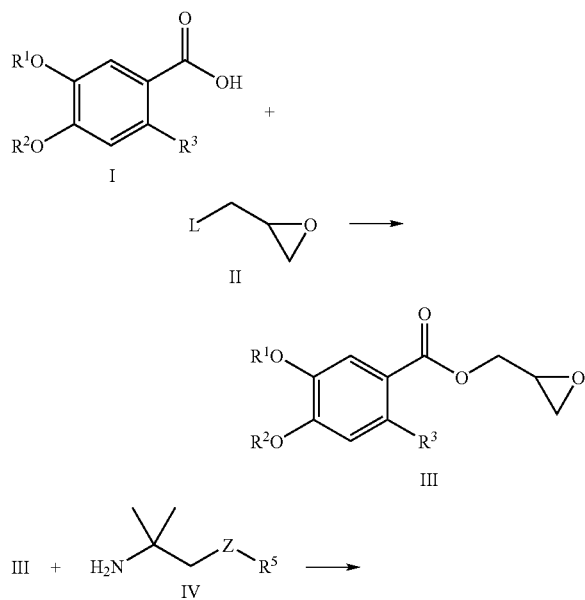

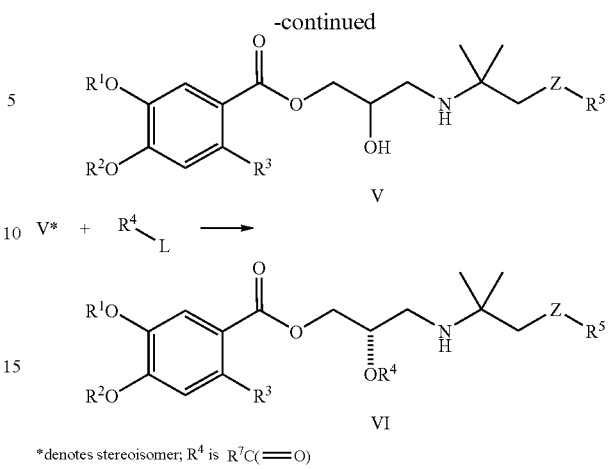

*denotes stereoisomer; $R^4$ is $R^7C(=\!\!=\!\!O)$

As described in greater detail below, the compounds of the invention may be used alone or in combination with other agents. For instance, a given compound of the invention may be used alone, or combined with one or more other compounds of the invention, or combined with non-beta blockers, such as carbonic anhydrase inhibitors (e.g. dorzolamide), such as miotics/parasympathomimetics (e.g. pilocarpine), prostaglandins (e.g. latanoprost), sympathomimetics (e.g. epinephrine), β-andrenergic blocking agents, hyperosmotic agents, $\alpha_2$ selective adrenergic agonists (e.g. brimonidine), or cannabinoids in regimens for the treatment of glaucoma. Likewise, in embodiments relating to non-ocular treatment, the compounds of the invention may be combined with other appropriate therapeutic agents in a regimen for such treatment.

Pharmaceutical compositions. According to another aspect of the invention, the compounds of the invention are formulated into compositions for application to the eye of patients in need of therapy. Thus, such compositions are adapted for pharmaceutical use as an eye drop, ointment, powder, solution, spray, or in contact lenses, inserts or the like, as described in greater detail below. Accordingly, formulation of compound into sterile water containing any desired diluents, salts, pH modifying materials and the like as are known to persons skilled in the pharmaceutical formulations art may be performed in order to achieve a solution compatible with administration to the eye. It may be that eye drops, inserts, contact lenses, gels and other topical liquid forms may require somewhat different formulations. All such formulations consistent with direct administration to the eye are comprehended hereby.

Formulations may contain the active compound, preferably in the form of a soluble acid addition salt, in amounts ranging from about 0.01% to about 10% by weight, preferably from about 0.1% to about 5% by weight. In an exemplary embodiment, a formulation contains compound 7 (Example 1) at a concentration ranging from about 0.05 to 3.0% w/v, more specifically from about 0.1 to 2.0% (w/v). Unit dosages of the active compound can range from about 0.01 to about 5.0 mg, preferably from about 0.05 to about 2.0 mg. The dosage administered to a patient will depend upon the patient's needs and the particular compounds employed, as would be readily understood and calculated by one of skill in the art.

Carriers used in the preparations of the present invention are preferably nontoxic ophthalmologically acceptable pharmaceutical organic or inorganic compositions such as water; mixtures of water and water-miscible solvents, such as lower alcohols; mineral oils; petroleum jellies; ethyl cellulose; polyvinylpyrrolidone and other conventional carriers. In addition, the pharmaceutical preparations may also contain additional components such as emulsifying, preserving, wetting and sterilizing agents. These include polyethylene glycols 200, 300, 400, and 600, carbowaxes 1,000, 1,500, 4,000, 6,000, and 10,000 bacteriocidal components such as quaternary ammonium compounds, phenylmercuric salts known to have cold sterilizing properties and which are non-injurious in use, thimerosal, methyl and propyl paraben, benzyl alcohol, phenyl ethanol, sorbic acid, buffering ingredients such as sodium chloride, sodium borate, sodium acetates, gluconate buffers, and other conventional ingredients such as sorbitan monolaurate, triethanolamine, oleate, polyoxyethylene sorbitan monopalmitylate, dioctyl sodium sulfosuccinate, monothioglycerol, thiosorbitol, ethylenediamine tetracetic acid, and the like. Additionally, suitable ophthalmic vehicles can be used as carrier media for the present purpose including conventional phosphate buffer vehicle systems, isotonic boric acid vehicles, isotonic sodium chloride vehicles, isotonic sodium borate vehicles and the like. The compositions or formulations may also contain solubilizing agents (e.g. glycerine) or chelating agents (e.g. EDTA for metal ions).

More particularly, the compositions may also have antioxidants in ranges that vary depending on the kind of antioxidant used. The usage also depends on the amount of antioxidant needed to allow at least 2 years shelf-life for the pharmaceutical composition. One or more antioxidants may be included in the formulation. Certain commonly used antioxidants have maximum levels allowed by regulatory authorities.

Reasonable ranges are about 0.01% to about 0.15% weight by volume of EDTA, about 0.01% to about 2.0% weight volume of sodium sulfite, and about 0.01% to about 2.0% weight by volume of sodium metabisulfite. One skilled in the art may use a concentration of about 0.1% weight by volume for each of the above. N-Acetylcysteine may be present in a range of about 0.01% to about 5.0% weight by volume, with about 0.1% to about 1% being preferred. Ascorbic acid or salt may also be present in a range of about 0.1% to about 5.0% weight by volume with about 0.5% to about 2% weight by volume preferred. Other sulfhydryls, if included, may be the same range as for N-acetylcysteine. Other exemplary compounds include mercaptopropionyl glycine, N-acetyl cysteine, β-mercaptoethylamine, glutathione and similar species, although other anti-oxidant agents suitable for ocular administration, e.g. ascorbic acid and its salts or sulfite or sodium metabisulfite may also be employed.

A buffering agent may be used to maintain the pH of eye drop formulations in the range of about 3.5 to about 8.0; this is necessary to prevent corneal irritation. Because the compounds of this invention are esters, the pH is preferably maintained at about 3.5 to about 6.0, preferably about 4.0 to about 5.5, in order to prevent hydrolysis of the ester bond and to ensure a good shelf life for the product.

The compositions of the present invention may also include tonicity agents suitable for administration to the eye. Among those suitable are mannitol, isotonic boric acid vehicles, isotonic sodium chloride vehicles, isotonic sodium borate vehicles and the like. For example, formulations of the present invention may be made approximately isotonic with 0.9% saline solution.

In certain embodiments, the ophthalmic compositions are formulated with viscosity enhancing agents. Exemplary agents are hydroxyethylcellulose, hydroxypropylcellulose, methylcellulose, and polyvinylpyrrolidone. The viscosity agents may exist in the compounds up to about 1.6% weight by volume. It may be preferred that the agents are present in a range from about 0.2% to about 1.0% weight by volume. A preferred range for polyvinylpyrrolidone may be from about 0.1% to about 0.2% weight by volume. One skilled in the art may prefer any range established as acceptable by the Food and Drug Administration.

The compounds of the invention may have co-solvents added if needed. Suitable co-solvents may include glycerin, polyethylene glycol (PEG), polysorbate, propylene glycol, and polyvinyl alcohol. The presence of the co-solvents may exist in a range of about 0.2% to about 1.0% weight by volume. It may also be preferred that polyvinyl alcohol may be formulated in the compounds of the invention in a range of about 0.1% to about 4.0% weight by volume. One skilled in the art may prefer ranges established as acceptable by the Food and Drug Administration.

Preservatives may be used in the invention within particular ranges. Among those preferred are up to 0.013% weight by volume of benzalkonium chloride, up to 0.013% weight by volume of benzethonium chloride, up to 0.5% weight by volume of chlorobutanol, up to 0.004% weight by volume or phenylmercuric acetate or nitrate, up to 0.01% weight by volume of thimerosal, up to about 0.2% sorbic acid, and from about 0.01% to about 0.2% weight by volume of methyl or propylparabens.

As noted above, Formula II encompasses both prodrugs and beta-blocking drugs. In another embodiment of the invention, the beta-blocking drugs described herein may be formulated for administration to parts of the body other than the eye. Other formulations for administration of the compositions of the present invention, wherein the delivery to the eye is not called for, may include tablets, liquids and sprays; intravenous, subcutaneous and intraperitoneal injectable solutions; compositions or devices for application to the skin, such as a patch or ointment; as well as enemas, suppositories, or aerosols.

As mentioned, the compounds of the invention may be used alone or in combination with other agents. Pharmaceutical compositions comprising combinations of compounds may be formulated in accordance with standard methodologies. Such combinations may include, for example, combinations of two or more compounds of the invention, or combinations of one or more compounds of the invention with non-beta blockers, such as carbonic anhydrase inhibitors (e.g. dorzolamide), such as miotics, parasympathomimetics (e.g. pilocarpine), prostaglandins (e.g. latanoprost), sympathomimetics (e.g. epinephrine), β-andrenergic blocking agents, hyperosmotic agents, $\alpha_2$ selective adrenergic agonists (e.g. brimonidine), or cannabinoids in regimens for the treatment of glaucoma. Likewise, in embodiments relating to non-ocular treatment, the compounds of the invention may be combined with other appropriate therapeutic agents in a composition for such treatment.

One embodiment of the invention comprises treatment of ocular hypertension with a combination of a compound of the invention and a prostaglandin derivative. Preferably, the combination provides a synergistic effect. More particularly, compounds of the invention are combined with at least one prostaglandin, such as Bimatoprost 0.03%, Latanoprost 0.005% and Travoprost 0.004% ophthalmic solutions, and their pharmaceutically acceptable analogues and derivatives. A preferred prostaglandin is Latanoprost. In exemplary formulations, the final composition concentration of a prostaglandin derivative is between about 0.001 and about 0.5 (w/v %), and the final composition concentration of the oculoselective beta-blocker or corresponding prodrug as described herein is between about 0.1 and about 1.0 (w/v %). A specific anti-glaucoma pharmaceutical preparation comprises a combination of a prostaglandin derivative and compound 7 (Example 1).

Another embodiment of the invention is directed to treatment of intraocular hypertension with a combination (preferably a synergistic combination) of a compound of the invention and a carbonic anhydrase inhibitor. Although both beta-blockers and carbonic anhydrase inhibitors are believed to lower IOP by decreasing the formation of aqueous humor, each of these classes of drugs operates by different mechanisms, such that the combination can provide a synergistic effect. A preferred carbonic anhydrase inhibitor is dorzolamide. In a specific embodiment, the final composition concentration of the carbonic anhydrase inhibitor derivative is between about 1.0 and about 5.0 (w/v %), and the final composition concentration of a compound of the invention, such as compound 7, is between about 0.1 and about 1.0 (w/v %).

In another embodiment, the invention is directed to treatment of ocular hypertension with a combination of a compound of the invention and a cannabinoid compound. The major active ingredient of marijuana, $\Delta^9$-terahydrocannabinol, has been known to exert a wide range of pharmacological effects, including reduction of intraocular pressure in glaucoma (Dewley, W. L. 1986, Pharmac. Rev. 38, 151-178). Novel cannabinoid (CB2) receptor agonists, their compositions, and the methods of their preparation are described in U.S. Pat. Nos. 5,605,906 and 5,532,237. The compounds have been shown to be useful for lowering IOP or treating glaucoma because of the activity on the cannabinoid receptor either by themselves or in combination with beta-blockers such as timolol. Recently a peripheral receptor for cannabinoids (CB2), that is not expressed in the brain but rather in macrophages in the marginal zone of spleen, has been isolated and characterized (Munro et al., 1993, Nature, 365, 61-65). Thus a selective CB2 agonist can have anti-inflammatory, analgesic, antiemetic, immunosuppressive and intraocular pressure reducing properties associated with cannabinoids without the psychoactive effects associated with CB1 receptors. It has been shown that certain 1,9-dihydroxy-octahydrobenzo-[c]quinolines (Johnson, U.S. Pat. No. 4,260,764; and Johnson, et al., U.S. Pat. No. 4,228,169) as well as the 9-oxo analogs (Belgian Pat. No. 854,655, 1977) are useful as CNS agents, especially as analgesics and tranquilizers, as hypotensives, diuretics and as agents for treatment of glaucoma. The corresponding 9-amino and 9-oximino analogs have also been shown to have similar properties (Johnson, U.S. Pat. No. 4,309,545). Any of these or other cannabinoids or derivatives can be utilized in the present embodiment. Preferably, the final composition concentration of the cannabinoid derivative is between about 0.001 and about 1.0 (w/v %), and the final composition concentration of the compound of the invention, such as compound 7, is between about 0.1 and about 1.0 (w/v %).

Another embodiment is directed to treatment of ocular hypertension with a combination (preferably synergistic) of a compound of the invention and pilocarpine. Preferably, the final composition concentration of the pilocarpine is between about 0.1 and about 1.0 (w/v %), and wherein the final composition concentration of the compound of the invention, such as compound 7, is between about 0.1 and about 1.0 (w/v %).

Yet another embodiment of the invention provides for treatment of ocular hypertension with a combination (preferably synergistic) of a compound of the invention and a clonidine derivative. Compounds having alpha-2 agonist activity are known to lower intraocular pressure. For example, the substituted 2-(arylimino) imidazolidines described in York, Jr., U.S. Pat. Nos. 4,461,904 and 4,517,199; and Cavero, et al., U.S. Pat. No. 4,515,800; are known to lower intraocular pressure. It is believed that these agents reduce intraocular pressure by suppressing the inflow of aqueous humor. Use of a combination of clonidine-type alpha-2 agonists such as apraclonidine (e.g., para-amino clonidine) or brimonidine and beta-blocker such as timolol to control intraocular pressure is described in DeSantis, U.S. Pat. No. 5,502,052. Preferably, the final composition concentration of the clonidine derivative is between about 0.05 and about 1.0 (w/v %), and the final composition concentration of the compound of the invention, such as compound 7, is between about 0.1 and about 1.0 (w/v %).

Another embodiment of the invention is directed to treatment of ocular hypertension with a combination (preferably synergistic) of a compound of the invention and epinephrine or dipivalylepinephrine (DPE). A preparation for reducing intraocular pressure consisting essentially of a therapeutically effective amount of the fixed combination of dipivalylepinephrine and beta-blocker is described in Gramer, U.S. Pat. No. 5,459,140. The use of two or more different types of drugs to lower elevated intraocular pressure has been a common practice, particularly in connection with patients who exhibit severe elevations in intraocular pressure and/or develop a resistance to the intraocular pressure lowering effect of a single drug. This practice has included combination therapy with a beta blocker and an alpha agonist. Reference is made to the following articles for further background in this regard: McGuinness, et al., "Timolol and Dipivalyl Epinephrine Combination Therapy", Aust. J. Ophthalmol., Vol. 10, pages 179-182 (1982); and Weineb, et al., "Effect of Adding Betaxolol to Dipivefrin Therapy", Am. J. Ophthalmol., Vol. 101, pages 196-198 (1986). In a preferred embodiment, the final composition concentration of the dipivalylepinephrine is between about 0.01 and about 0.25 (w/v %), and the final composition concentration of the compound of the invention, such as compound 7, is between about 0.1 and about 1.0 (w/v %).

Administration. Compositions comprising the compounds of the invention may be delivered to the eye of a patient in one or more of several delivery modes known in the art. In a preferred embodiment, the compositions are topically delivered to the eye in eye drops or washes. In another embodiment, the compositions may be delivered to various locations within the eye via periodic intraocular injection or by infusion in an irrigating solution such as BSS® or BSS PLUS® (Alcon USA, Fort Worth, Tex.) or by using pre-formulated solutions of the beta-blocker in excipients such as BSS® or BSS PLUS®. This embodiment will have particular utility for drug delivery to prevent IOP spikes during or after surgical procedures.

Alternatively, the compositions may be applied in other ophthalmologic dosage forms known to those skilled in the art, such as pre-formed or in situ-formed gels or liposomes, for example as disclosed in Herrero-Vanrell, U.S. Pat. No. 5,718,922. In another embodiment, the composition may be delivered to or through the cornea of an eye in need of treatment via a contact lens (e.g. Lidofilcon B, Bausch & Lomb CW79 or DELTACON (Deltafilcon A) or other object temporarily resident upon the surface of the eye. In other embodiments, supports such as a collagen corneal shield (e.g. BIO-COR dissolvable corneal shields, Summit Technology, Watertown, Mass.) can be employed. The compositions can also be administered by infusion into the eyeball, either through a cannula from an osmotic pump (ALZET®, Alza Corp., Palo Alto, Calif.) or by implantation of timed-release capsules (OCCUSENT®) or biodegradable disks (OC- ULEX®, OCUSERT®) which contain the compositions. These routes of administration have the advantage of providing a continuous supply of the composition to the eye.

Several other types of delivery systems are available that are particularly suitable for delivering pharmaceutical compositions to the interior or posterior of the eye. For instance, Parel, et al., U.S. Pat. No. 6,154,671 discloses a device for transferring a medicament into the eyeball by iontophoresis. The device utilizes a reservoir for holding the active agent, which contains at least one active surface electrode facing the eye tissue lying at the periphery of the cornea. The reservoir also has a return electrode in contact with the patient's partly closed eyelids. Wong, et al, U.S. Pat. No. 5,869,079 discloses combinations of hydrophilic and hydrophobic entities in a biodegradable sustained release ocular implant. In addition, Guo et al., U.S. Pat. No. 6,375,972, Chen et al., U.S. Pat. No. 5,902,598, Wong, et al., U.S. Pat. NO. 6,331,313, Ogura et al., U.S. Pat. No. 5,707,643, Weiner, et al., U.S. Pat. No. 5,466,233, and Avery, et al., U.S. Pat. No. 6,251,090 each describes intraocular implant devices and systems that may be used to deliver pharmaceutical compositions comprising compounds of the present invention.

As noted above, some of the compounds of this invention will be useful in fields broader than ophthalmology. These areas will include indications for which short-acting beta-blockers are typically utilized, for example, lowering blood pressure, relief of angina, treatment of congestive heart failure and arrhythmias and treatment of post-trauma or post-operative ischemia, as well as the neuroprotective applications referred to above. Other routes of administration of the compositions of the present invention, wherein the delivery to the eye is not called for, may include oral or intranasal delivery; intravenous, subcutaneous and intraperitoneal injection; and transdermal or transmucosal delivery, as would be understood by one of skill in the art.

For effective treatment of glaucoma or any of the other diseases or conditions referred to herein, one skilled in the art may recommend a dosage schedule and dosage amount adequate for the subject being treated. The dosing may occur less frequently if the compositions are formulated in sustained delivery vehicles, or are delivered via implant. For topical delivery to the eye, it may be preferred that dosing occur one to four times daily for as long as needed. The dosage amount may be one or two drops per dose. The dosage schedule may also vary depending on the active drug concentration, which may depend on the particular beta-blocker used and on the needs of the patient. In addition, compositions comprising compounds of the invention may be administered in a combination regimen with one or more other therapeutic agents, as mentioned above and as would be apparent to one of skill in the art. In this embodiment, it will be appreciated that combination therapy may be performed by administering two or more different therapeutic compounds together as a single pharmaceutical composition, or separately in different pharmaceutical compositions and/or in a different dosage form or regimen.

Additional advantages and novel features of this invention will become apparent to those skilled in the art upon study of the following examples, which are not intended to be limiting.

EXAMPLES

All compounds may be prepared as free base or acid salt forms. Generally, experimental preparation provide the acid salt unless otherwise indicated.

Standard Free Base and Acid Salt Preparation Methods

Typical method for the preparation of free base: 0.1 g of the oxalate salt or the hydrochloride salt was suspended in 50 mL ethyl acetate and shaken with 100 mL saturated potassium carbonate for 1 minute. The ethyl acetate layer was separated and washed with 50 mL brine, dried over magnesium sulfate, dried, filtered and used as is in the next step.

Typical method for the preparation oxalate salt: To a solution of free base(from above experiment) in 20 mL ethyl acetate, a saturated solution of oxalic acid in ethyl acetate was added dropwise until a pH of 2 was obtained and the salt was allowed to crystallize. The crystallized salt was then filtered, washed with ethyl acetate and dried before using.

Typical method for the preparation hydrochloride salt: To a solution of free base(from above experiment) in 20 mL ethyl acetate a 1M hydrogen chloride in anhydrous ether was added dropwise until a pH of 2 was obtained and the salt was allowed to crystallize. If no crystals were obtained, then either anhydrous diethyl ether or isopropyl ether was added until the solution became cloudy. The crystallized salt was then filtered, washed with ethyl acetate and dried before using.

Typical method for the preparation of other acid salts: Other acids described herein may be contacted with compounds of the invention to provide complexes of, or acid salts or pharmaceutically acceptable salts of the compounds of the invention using methods similar to those described hereinabove. For example, compound 7 was treated individually with sulfuric, succinic, maleic, fumaric, or tartaric acid to provide the corresponding salt. Table A provides a few non-limiting examples of some acid salts prepared employing the above methods.

TABLE A

| Structure | m.p. |
| --- | --- |
| 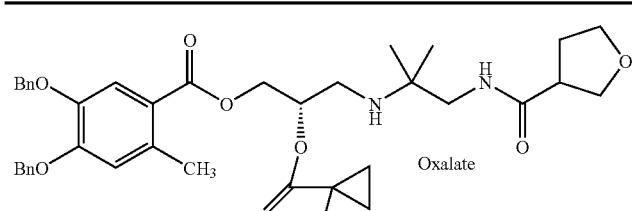 | 161.2-162.2° C. |

TABLE A-continued

| Structure | m.p. |
|---|---|
| [Structure with Oxalate] | 132.0-135.4° C. |
| [Structure with Fumarate] | 164.3-168.2° C. |
| [Structure with Tartarate] | 102.1-104.4° C. |

Example 1

Synthesis of Compound 7

Step 1 Synthesis of 4,5-bis-benzyloxy-2-methyl-benzoic acid 2-(1-methyl-cyclopropanecarbonyloxy)-3-{1,1-dimethyl-2-[(tetrahydro-furan-3-carbonyl)-amino]-ethylamino}-propyl ester [Intermediate 2] as its hydrochloride salt The synthesis of Intermediate 1 is described in Patil, et al., U.S. Pat. Nos. 4,897,417 and 4,966,914, disclosures of which are hereby incorporated herein by reference, in their entireties. To a suspension of 4,5-bis-benzyloxy-2-methyl-benzoic acid 3-{1,1-dimethyl-2-[(tetrahydro-furan-3-carbonyl)-amino]-ethylamino}-2-hydroxy-propyl ester [Intermediate 1 (10 g, 14.7 mmoles )] in dry acetonitrile (130 mL) under nitrogen atmosphere was added freshly distilled 1-methylcyclopropylcarbonyl chloride (7.15 g, 60 mmoles). The resulting clear solution was refluxed for 16 hours and then evapo-

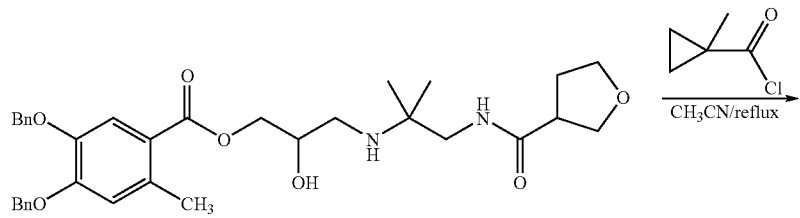

Intermediate 1

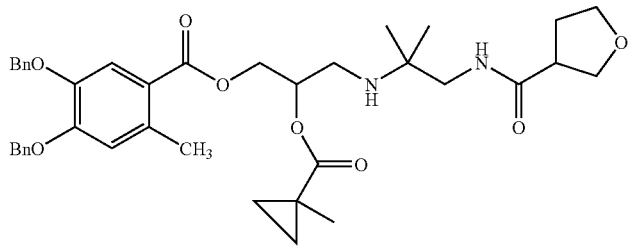

Intermediate 2 rated to give an oil. To this residue was added n-hexane (100 mL). The mixture was stirred at 55° C. for 30 min and the hexane layer was decanted while the solution was hot. This procedure was repeated twice. The thick residue was washed with ether and dried in vacuo to give Intermediate 2, (11 g)] as its hydrochloride salt. The NMR spectra and the elemental analysis (carbon, hydrogen and nitrogen) were consistent with the assigned structure.

Step 2 4,5-Dihydroxy-2-methyl-benzoic acid 3-{1,1-dimethyl-2-[(tetrahydro-furan-3-carbonyl)-amino]-ethylamino}-2-(1-methyl-cyclopropanecarbony-loxy)-propyl ester Compound 7

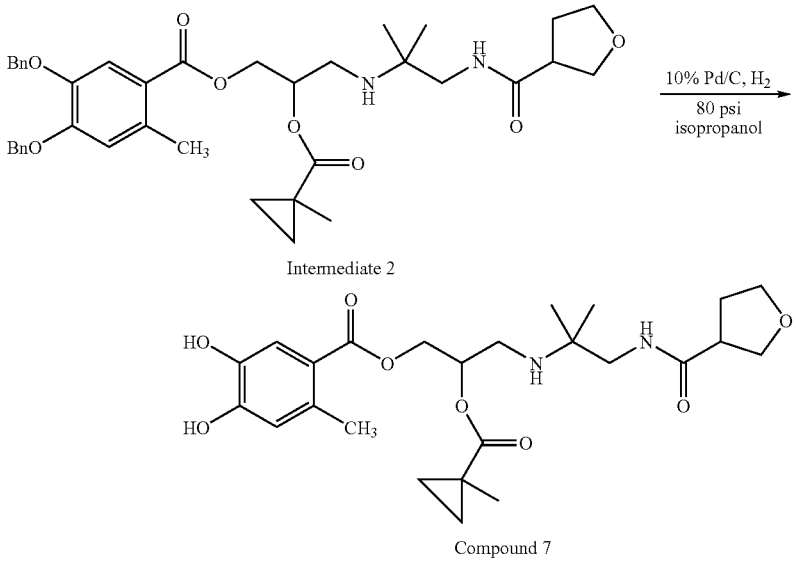

A mixture containing Intermediate 2 as its hydrochloride salt ( Step 1, 10 g) and 10% palladium on charcoal (1 g) in isopropyl alcohol (300 mL) was hydrogenated in a Parr apparatus at 80 psi for 20 hours. The reaction mixture was filtered over a bed of celite and evaporated to dryness. The residue was dissolved in ethanol (50 mL). The ethanolic layer (pH=7) was acidified with 1M hydrochloric acid in ether to a pH ~2 and again evaporated to dryness to give a white foam. This foam was treated with ethyl acetate and stirred for 30 minutes. Ether was subsequently added to this mixture to give Compound 7 as a white solid (6.8 g). The NMR spectra and the elemental analysis (carbon, hydrogen and nitrogen) were consistent with the assigned structure.

Example 2

Synthesis of Compound 8

Step 1 Synthesis of 4,5-Bis-benzyloxy-2-methyl-benzoic acid 2-(2,2-dimethyl-cyclopropanecarbony-loxy)-3-{1,1-dimethyl-2-[(tetrahydro-furan-3-carbonyl)-amino]-ethylamino}-propylester [Intermediate 3] as its hydrochloride salt

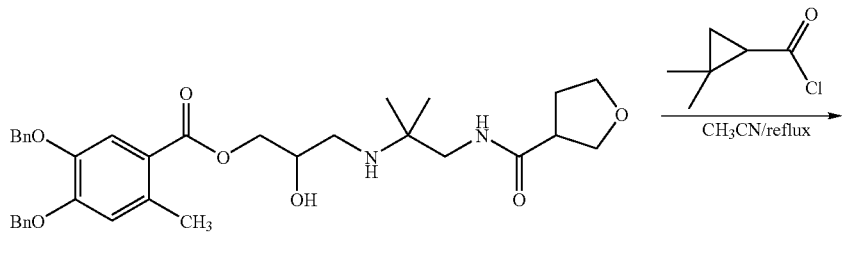

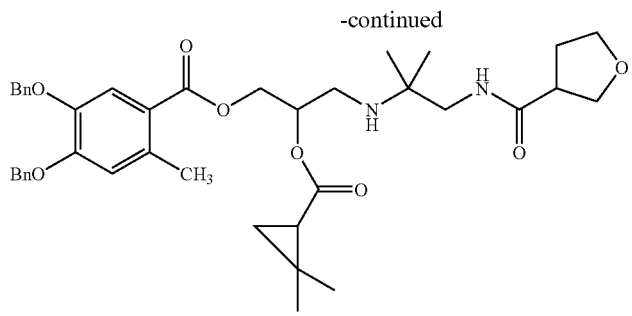

Intermediate 3

To a suspension of Intermediate 1 (3.66 g,5.38 mmoles) in dry acetonitrile (35 mL) under nitrogen atmosphere was added freshly distilled 2,2-dimethylcyclopropylcarbonyl chloride (2.12 moles, 16 mmoles). The resulting clear solution was refluxed for 3 days and then evaporated to dryness. The residue was dissolved in chloroform (200 mL) and washed with saturated potassium carbonate and brine. The chloroform layer was dried (MgSO4) and evaporated. This mixture was purified by silica gel column chromatography to give Intermediate 1 in free base form as a white powder, which was dissolved in acetone and acidified with 1M hydrochloric acid in ether until a pH of 2 was realized. Additional ether was added until the solution turned cloudy. The resulting white salt was isolated by decanting the supernatant and was dried under high vacuum to give Intermediate 3 as a white foam (900 mg). The NMR spectra and the elemental analysis (carbon, hydrogen and nitrogen) were consistent with the assigned structure.

Step 2 Synthesis of 4,5-dihydroxy-2-methyl-benzoic acid 2-(2,2-dimethyl-cyclopropanecarbonyloxy)-3-{1,1-dimethyl-2-[(tetrahydro-furan-3-carbonyl)-amino]-ethylamino}-propyl ester [Compound 8]

The free base of Intermediate 3 was converted to its corresponding oxalate salt as described above. A mixture containing Intermediate 3 as an oxalate salt (200 mg) and 10% palladium on charcoal (100 mg) in isopropyl alcohol (30 mL) was hydrogenated in a Parr apparatus at 60 psi for 12 hours. Completeness of the reaction was confirmed by TLC (Intermediate 3: TLC in 5% Methanol in methylene chloride containing 1 drop of conc. ammonia, RF 0.5; Compound 8, (10% methanol in methylene chloride containing 1 drop of conc. ammonia Rf 0.3). The reaction mixture was filtered over a bed of celite, evaporated to dryness and triturated with ether until a semi-solid was formed. The ether layer was decanted and the semi-solid was subjected to high vacuum to obtain Compound 8 as a white foam (68 mg). The NMR spectra and the elemental analysis (carbon, hydrogen and nitrogen) were consistent with the assigned structure.

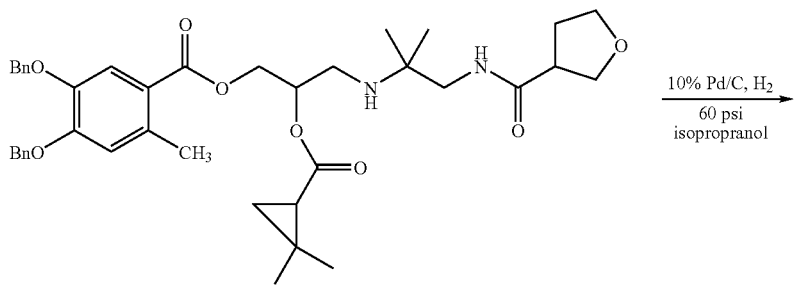

Intermediate 3

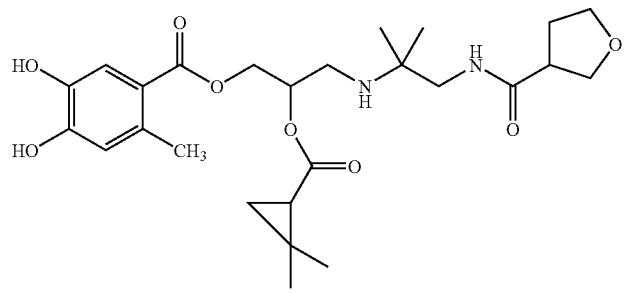

Compound 8

Example 3

Synthesis of Compound 9

Step 1 Synthesis of 4,5-bis-benzyloxy-2-methyl-benzoic acid 3-{1,1-dimethyl-2-[(tetrahydro-furan-3-carbonyl)-amino]-ethylamino)}-2-(2-methoxymethyl-cyclopropanecarbonyloxy)-propyl ester [Intermediate 4].

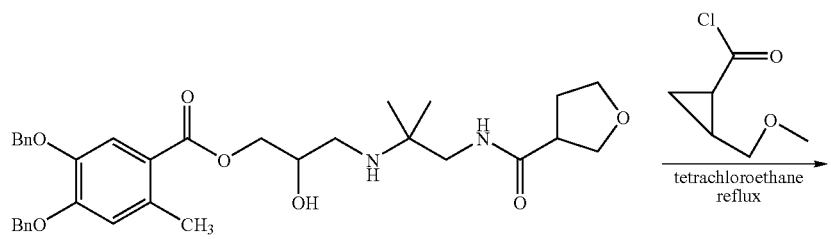

Intermediate 1

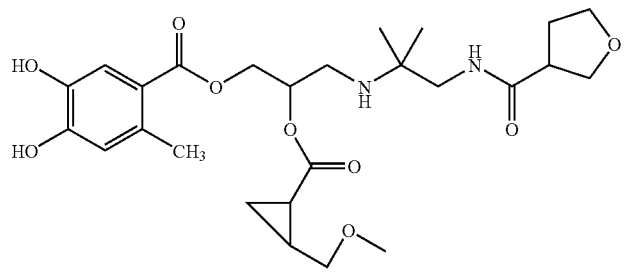

Intermediate 4

Freshly distilled 2-methoxymethylcyclopropylcarbonyl chloride (0.891 g, 6 mmoles) was added to a suspension of Intermediate 1 (1.02 g, 1.5 mmoles) in dry tetrachloroethane (35 mL) under nitrogen atmosphere. The reaction mixture was refluxed for 30 minutes and evaporated to dryness under high vacuum. The residue was suspended in toluene, evaporated to dryness in vacuo and the residue obtained was dissolved in ethyl acetate and washed with saturated. sodium carbonate and brine. The organic layer was dried (MgSO₄) and evaporated. This mixture was purified by silica gel column chromatography using chloroform:methanol:ammonia (1:19:0.1) to give Intermediate 4 in free base form as a white powder (1.58 g), which was dissolved in ethyl acetate (5 mL) and to this was added ether (50 mL). The gum that settled out was isolated and dried in vacuo to give a foam (0.518 g). The NMR spectra and the elemental analysis (carbon, hydrogen and nitrogen) were consistent with the assigned structure.

Step 2 Synthesis of 4,5-dihydroxy-2-methyl-benzoic acid 3-{1,1-dimethyl-2-[(tetrahydro-furan-3-carbonyl)-amino]-ethylamino}-2-(2-methoxymethyl-cyclopropanecarbonyloxy)-propyl ester [Compound 9] (as its oxalate salt)

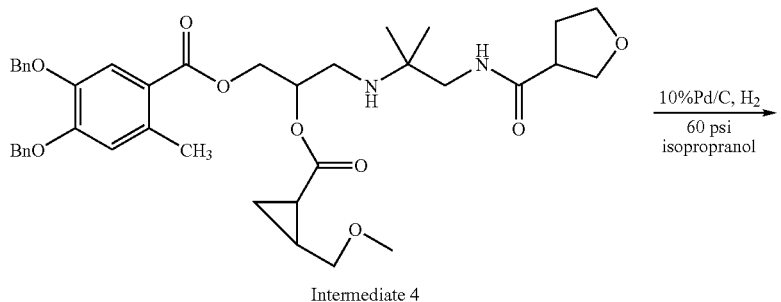

Intermediate 4

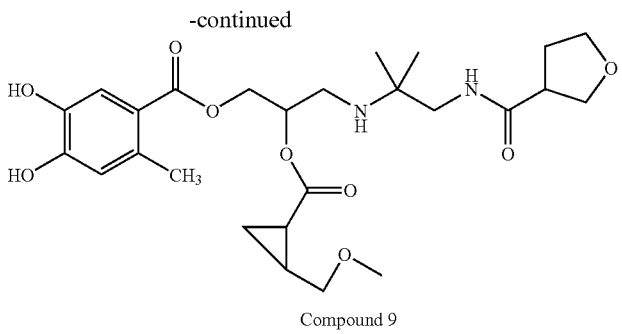

Compound 9

To a mixture containing Intermediate 4 as an oxalate salt (518 mg) and 10% palladium on charcoal (100 mg) in ethyl alcohol (50 mL) was hydrogenated in a Parr apparatus at 60 psi for 12 hours. The reaction mixture was filtered over a bed of Celite, evaporated to dryness and triturated with ether until a solid formed. The ether layer was decanted and the solid was subjected to high vacuum to obtain Compound 9 as a white foam (354 mg). The NMR spectra and the elemental analysis (carbon, hydrogen and nitrogen) were consistent with the assigned structure.

Example 4

Synthesis of Compound 12

(S)-4,5-Bis-benzyloxy-2-methyl-benzoic acid oxiranylmethyl ester.

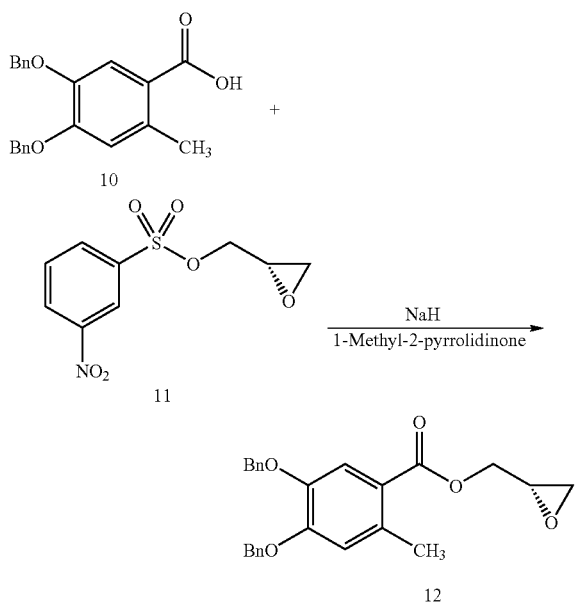

Under a nitrogen atmosphere, Sodium hydride (5.5 g, 60% suspension in oil) was added to an iced-cooled solution of 4,5-bis-benzyloxy-2-methyl-benzoic acid [10, 40 g, 0.11 moles) in 1-methyl-2-pyrrolidinone (80 mL) and stirred for 30 minutes. To this was then added 2-(S)-glycidylnosylate (11, 38.7 g, 0.15 moles, Aldrich Chemical Company, Milwaukee, Wis.) and stirred for 20 hours. Water (800 mL) was then added to the reaction mixture, and the resultant was extracted with ethyl acetate (4×200 mL), washed with brine (200 mL), dried over sodium sulfate and evaporated to dryness to give an off-white solid which was then recrystallized from ethyl acetate to give 12 (41.2 g, 88.7%). (TLC, Rf=0.8, 1.6% methanol in methylene chloride). The NMR and IR were consistent with the assigned structure.

Example 5

Synthesis of Compounds 14a and 14b (S)-4,5-bis-benzyloxy-2-methyl-benzoic acid 2-hydroxy-3-(2-hydroxy-1,1-dimethyl-ethylamino)-propyl ester as the oxalate or hydrochloride salt(14a and 14b, respectively).

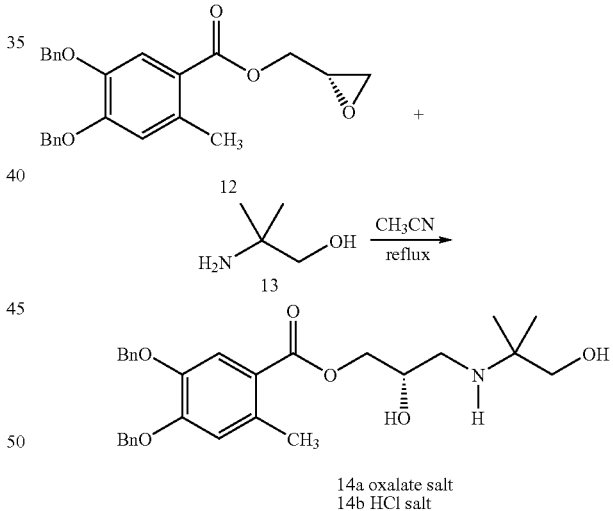

14a oxalate salt
14b HCl salt

A mixture of epoxide 12 (24.66 g, 0.061 mole) and aminoalcohol 13 (13 g, 0.146 mole) in anhydrous acetonitrile (dried over 4 Å molecular sieves) was refluxed for 48 hours and evaporated to dryness under reduced pressure. The resulting residue was dissolved in ethyl acetate (300 mL) and washed with brine (4×100 mL), dried over sodium sulfate and evaporated to dryness under reduced pressure. The residue was re-dissolved in ethyl acetate, acidified with oxalic acid in ethyl acetate and allowed to crystallize. The solid was filtered and dried in vacuo to give 20.1 g (56.5%) of crude 14a. The crystalline solid 14a (17.6 g) was converted to its free base form and chromatographed on a silica gel column using 5% methanol/methylene chloride as eluent to give the free base as an oil, which was dissolved in ether and acidified with HCl/ether, evaporated to dryness and placed in high vacuum to give 14b as a white foam. The NMR and IR were consistent with the assigned structure.

Example 6

Synthesis of Compound 15

(S)-4,5-dihydroxy-2-methyl-benzoic acid 2-hydroxy-3-(2-hydroxy-1,1-dimethyl-ethylamino)-propyl ester as its hydrochloride salt.

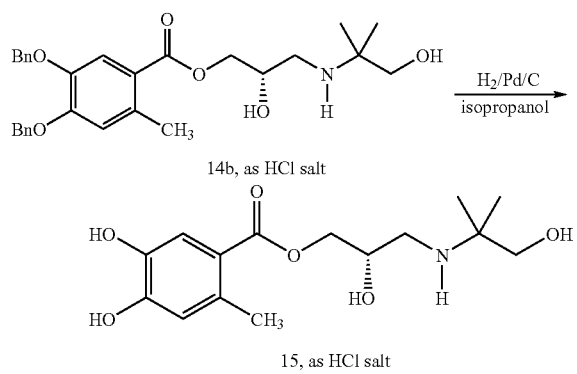

10% Pd/C (300 mg) was added to a solution of 14b (3.0 g, 9.43 mmole) in isopropanol (100 mL) and hydrogenated in a Parr Hydrogenation Shaker at 70 psi for 6 hours. The reaction mixture was then filtered, acidified with HCl/ether and evaporated under reduced pressure to give a yellow gum. The title compound 15 (0.8 g) was obtained from this gum upon crystallization from a mixture of ethyl acetate (20 mL) and isopropanol (10 mL). The NMR and IR spectra and the elemental analysis (carbon, hydrogen and nitrogen) were consistent with the assigned structure.

Example 7

Synthesis of Compound 16

(S)-4,5-bis-benzyloxy-2-methyl-benzoic acid 3-[2-(2,2-dimethyl-propionyloxy)-1,1-dimethyl-ethylamino]-2-hydroxy-propyl ester.

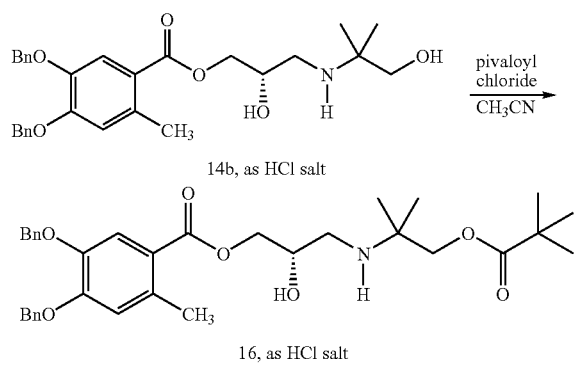

A mixture of the amino-diol 14b (6.4 g, 0.012 mole) and pivaloyl chloride, (1.9 g, 0.016 mole) in anhydrous acetonitrile (100 mL, dried over 4 Å molecular sieves), was refluxed for 16 hours and evaporated to dryness. The residue was treated with hexane and decanted. The remaining oil after decantation of the hexane layer was dissolved in 200 mL ethyl acetate and washed with sat. potassium carbonate, washed with brine and dried to give 16 as its free base form and chromatographed on a silica gel column using 1% methanol in methylene chloride. The oil was acidified with HCL/Ether to give 3.2 g as foam. TLC in 5% methanol in methylene chloride showed a single homogeneous spot at Rf=0.25). NMR and IR were consistent with the assigned structure.

Example 8

Synthesis of Compound 17

(S)-4,5-bis-dihydroxy-2-methyl-benzoic acid 3-[2-(2,2-dimethyl-propionyloxy)-1,1-dimethyl-ethylamino]-2-hydroxy-propyl ester.

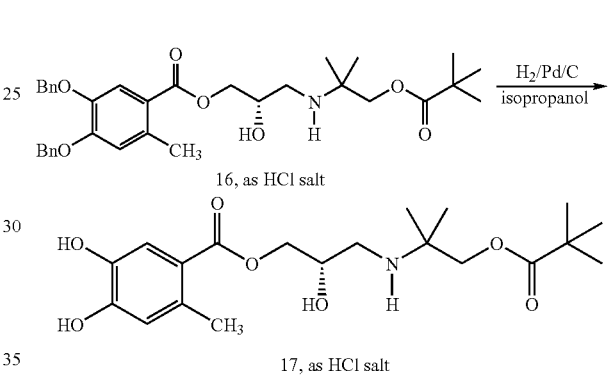

A mixture of 16 (1.0 g, 1.63 mmole) and 10% Pd/C (100 mg) in acetic acid (100 mL) was hydrogenated in a Parr hydrogenation apparatus at 80 psi for 60 minutes, filtered and evaporated to dryness and subsequently co-evaporated with toluene. The residue was redissolved in isopropanol, the insoluble material was filtered out and the solution was concentrated under reduced pressure. The resultant gum was triturated with hexane and the hexane layer was decanted. This trituration procedure was repeated with ether and the residue obtained after decanting the ether was dried under high vacuum to give 17 as a white foam (0.6 g, 85%).

Example 9

Synthesis of Compound 18

(S)-Tetrahydro-furan-3-carboxylic acid 2-[3-(4,5-bis-benzyloxy-2-methyl-benzoyloxy)-2-hydroxy-propylarnino]-2-methyl-propyl ester (18).

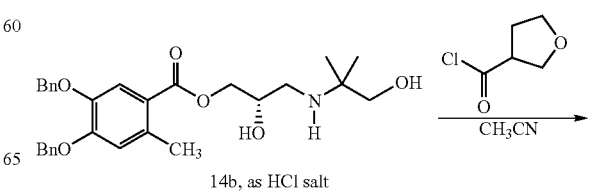

-continued

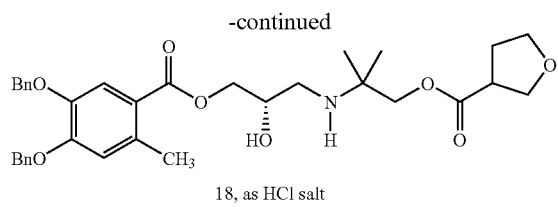

18, as HCl salt

A mixture of the amino-diol 14b (5.26 g, 8.92 mmole) and 3-tetrahydrofurancarbonyl chloride, (1.7 g, 12.86 mmole) in anhydrous acetonitrile (100 mL, dried over 4 Å molecular sieves), was stirred at room temperature for 16 hours and evaporated to dryness. The residue was treated with ether and a white solid precipitated. The ether supernatant was decanted and the solid was recrystallized from isopropanol (20 mL) to give 18 (270 mg) as a white crystalline solid. The NMR and IR spectra and the elemental analysis (carbon, hydrogen and nitrogen) were consistent with the assigned structure.

Example 10

Synthesis of Compound 19

(S)-Tetrahydro-furan-3-carboxylic acid 2-[3-(4,5-dihydroxy-2-methyl-benzoyloxy)-2-hydroxy-propylamino]-2-methyl-propyl ester.

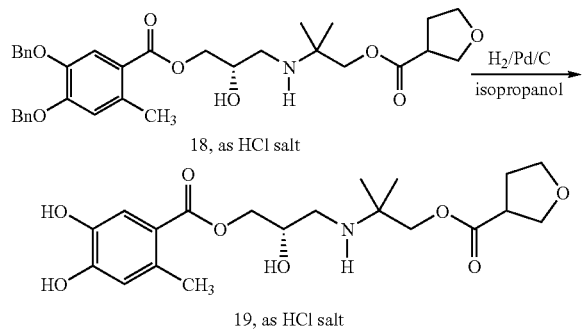

A mixture of 18 (570 mg, 0.91 mmole) and 10% Pd/C (100 mg) in isopropanol (50 mL) was hydrogenated in a Parr hydrogenation apparatus at 80 psi for 60 minutes, filtered and evaporated to dryness and acidified with HCl/ether. The residue was triturated with ethyl acetate to give a gum. The ethyl acetate layer was decanted and the yellow gum was subjected to high vacuum to give 19 as a yellow foam (440 mg).

Example 11

Synthesis of Compound 21

(S)-4,5-bis-benzyloxy-2-methyl-benzoic acid 3-(2-tert-butoxy-1,1-dimethyl-ethylamino)-2-hydroxy-propyl ester.

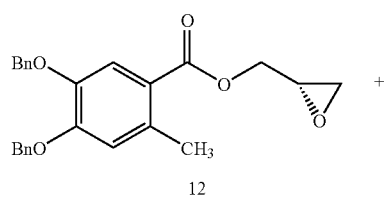

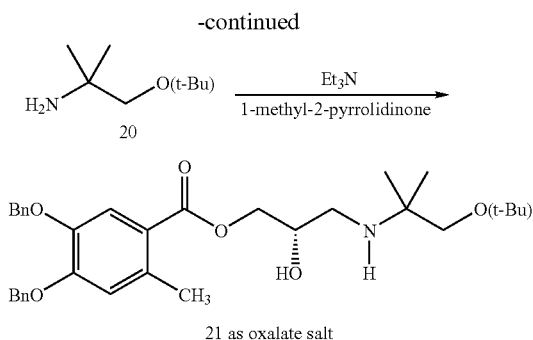

21 as oxalate salt

A mixture of epoxide 12 (2.47, 6.1 mmole), amino-alcohol 20 (1.62 g, 6.7 mmole) and triethylamine (1.36 mL, 13.4 mmole) in anhydrous 1-methyl-2-pyrrolidinone(dried over 4 Å molecular sieves) was heated at 80° C. for 48 hours and evaporated to dryness under high vacuum. The resulting solid was suspended in ethyl acetate (300 mL) and washed with sodium carbonate, brine, dried over sodium sulfate and evaporated to dryness under reduced pressure. The residue was re-dissolved in ethyl acetate, acidified with oxalic acid in ethyl acetate and filtered to remove any the insoluble solid. Ether was added to the filtrate to provide a solid which was recrystallized from isopropanol, filtered and dried in vacuo to give 21 (0.9 g, 1.4 mmole). The NMR and IR were consistent with the assigned structure.

Example 12

Synthesis of Compound 22

(S)-4,5-dihydroxy-2-methyl-benzoic acid 3-(2-tert-butoxy-1,1-dimethyl-ethylamino)-2-hydroxy-propyl ester.

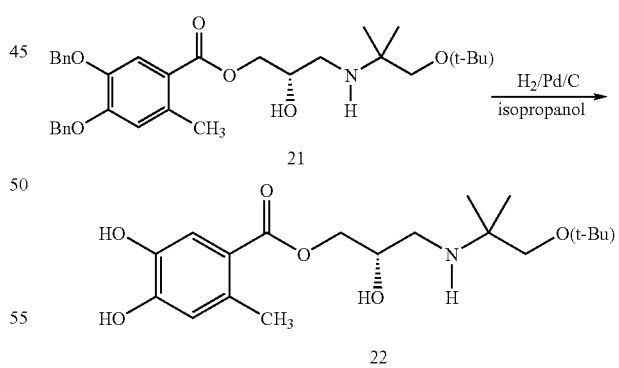

A mixture of 21 (820 mg, 1.25 mmole) and 10% Pd/C (100 mg) in 2-propanol (50 mL) was hydrogenated in a Parr hydrogenation apparatus at 50 psi for 16 h, filtered and evaporated to dryness and acidified with HCl/ether. The residue was triturated with 20 mL ethyl acetate to give a gum. The ethyl acetate layer was decanted. This process was repeated five times and the resulting gum was subjected to high vacuum to give 22 as a foam (38 mg). TLC in 5% methanol in methylene chloride showed a single homogeneous spot at Rf=0.5). NMR and IR were consistent with the assigned structure.

Example 13

Binding Efficacy of Selected Compounds of the Invention

Human recombinant adrenergic beta-1 Assays (Radioligand Binding) were conducted according to the procedure described by Feve, B., et al., Proc. Natl. Acad. Sci. USA, 91, 5677, 1994 using [[$^{125}$I]] ) Cyanopindolol as a radioligand. The results are expressed in $IC_{50}$ (nM).(Table B)

TABLE B

| Compound number | R | Binding efficacy $IC_{50}$ (nM) |
|---|---|---|
| 15 | H | 39 |
| 17 | (pivaloyl group) | 12 |
| 19 | (tetrahydrofuranyl carbonyl group) | 6.4 |

Example 14

Evaluation of Ocular Irritation

Thirty albino rabbits were randomly divided into five groups. Each rabbit was dosed in the conjunctival sac of the right eye topically every ten minutes for one hour (six doses) with 50 μL of 0.0%, 0.3%, 0.5%, 1.0% and 2% of test compound, in 0.9% saline solution. The treated eye of each rabbit was examined for indications of ocular irritation, including swelling, discharge, redness, iritis of conjunctiva, eyelid, iris as well as opacity and involvement of the cornea. Individual scores were added to determine the degree of slight, moderate or severe irritation. Ocular observations were made before the treatment, one hour after the first and sixth instillation and then 1, 2, 3, 4 and 7 days, using a slit lamp.

Results: Compound 7 (Example 1) was compared with a compound of the formula below, referred to hereinafter as "compound 6," and disclosed in Patil, et al., U.S. Pat. Nos. 4,897,417 and 4,966,914.

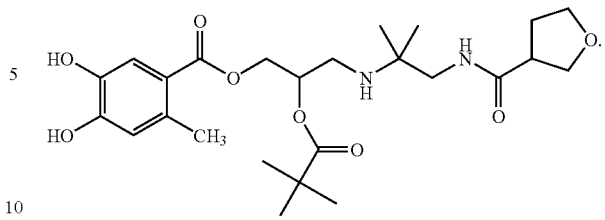

When compound 7 was applied topically, no ocular irritation was observed with dosing six times every ten minutes at 0.3%, 0.5%, 1.0% and 2.0% in the right conjunctival sac of albino rabbits compared to a control group dosed with 0.9% saline. However compound 6 showed moderate irritation at 1% concentration.

Example 15

Corneal Anesthesia Measurements

The effect of a 50 μl single instillation of 0.3%, 0.5%, 1.0% and 2.0% solution of compound 7 on corneal anesthesia, after a single instillation in the conjunctival sac of the right eyes of albino rabbits (N=5) was measured using a Cochet's esthesiometer (nylon thread: 0.12 mm diameter, 10 mm long). Corneal anesthesia was evaluated by the number of corneal mechanical stimuli necessary to induce a blinking reflex. The effect of drug solutions was compared with sterile 0.9% NaCl treated animals (control group) and 0.4% oxybuprocaine (Novesine®).

Results: The compound 7 exhibited no corneal sensitivity (local anesthetic activity) compared to 0.4% oxybuprocaine, whereas compound 6 exhibited complete corneal sensitivity loss at 1%.

Example 16

Stability Tests

An accelerated stability test was conducted on 0.25% solutions of compounds 6, 7, and 8 (Example 2) at 40° C. for 1, 2, 3, 4, 8 and 12 weeks and monitored for the disappearance of the prodrugs and appearance of the parent compound by HPLC analysis. The parent compound (referred to hereinafter as compound 4) has the formula:

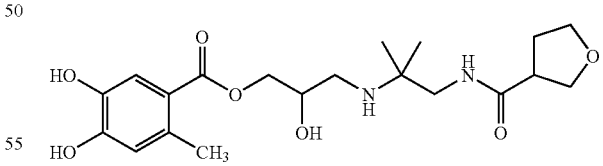

The respective compounds were dissolved in an acetate buffer, pH 3.5 (0.018% sodium acetate, 0.135% acetic acid, 0.9% sodium chloride in water for injection) to obtain 0.25% solution. The stability of the compounds was determined at 40° C. for 1, 2, 3, 4, 8, and 12 weeks. The concentration of the parent compound as well as the concentrations of the prodrug compounds 6, 7, and 8 at each time point by HPLC method.

Results: As shown in FIG. 1, compound 7 is most stable at 40° C. at pH 3.5 as compared to the compounds 6 and 8. A conventional eye drop formulation of compound 7 has a projected shelf-life of at least 18 months at room temperature, and a formulation of compound 8 has 7.9 months projected shelf life, whereas compound 6 has only 2.6 months of projected shelf-life at room temperature.

Example 17

Ocular Bioavailability

Three rabbits were used per time point. The 50 μl test substance was administered in a single instillation using a micropipette into the conjunctival sac of the right and the left eyes. The rabbits were anesthetized with an intramuscular injection of Imalgéne® 1000 (ketamine 32 mg/kg), and Rompun® (xylasine 7.5 mg/kg). They were then desanguinated by cardiac puncture and thereafter euthanized by an overdose of pentobarbital. Immediately after death, the eyes were microdissected to obtain: cornea (C), aqueous humor (AH), and iris-ciliary body (ICB). All samples were stored at −80° C. Only aqueous humor (AH) samples were analyzed by HPLC.

Figure 2:
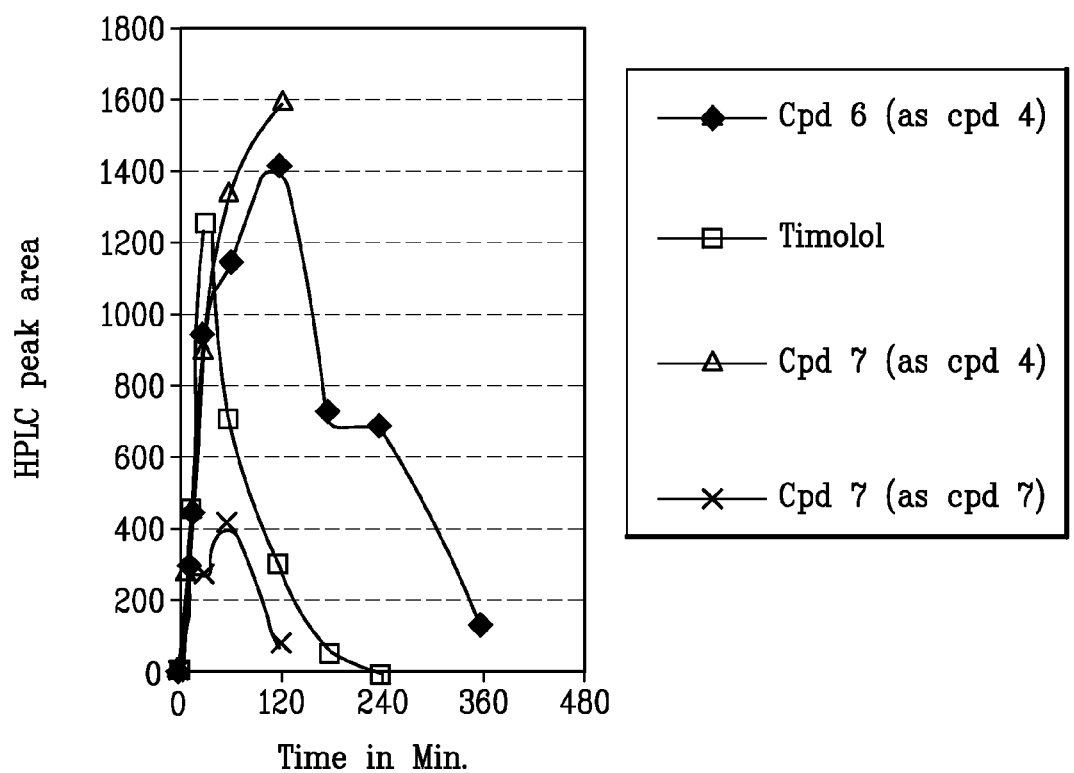
FIG. 2 is a graph showing a time course of the ocular penetration of timolol (-■-), compound 6 (-▲-), compound 7 (-X-) and the parent compound formed from compounds 6 and 7 (compound 4, -♦-).

Results: As can be seen in FIG. 2, compound 7 is rapidly absorbed across the cornea and metabolized to the parent compound 4 in appreciably higher quantities as compared to compound 6. It should be noted that some of prodrug compound 7 itself is also present in aqueous humor, whereas levels of compound 6 were below the detection limit of the HPLC method.

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

What is claimed:

1. A compound of Formula I:

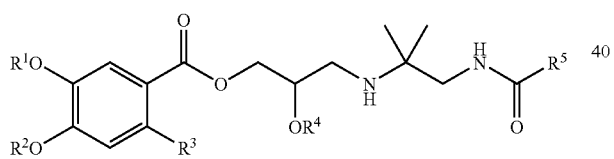

wherein:
$R^1$ and $R^2$ are each independently H, W, or a phenoxyl protecting group;
$R^3$ is hydrogen, straight chain or branched $C_1$-$C_{10}$ alkyl, cycloalkyl, amino, or $C_1$-$C_{10}$ alkoxy;
$R^4$ is H or W, provided that at least one of $R^1$, $R^2$, and $R^4$ is W;
$R^5$ is tetrahydrofuranyl,;
W is:

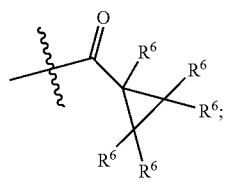

and
each $R^6$ is independently H, straight chain or branched $C_1$-$C_{10}$ alkyl, or straight chain or branched $C_1$-$C_{10}$ alkoxyalkyl;
or a stereoisomer or pharmaceutically acceptable salt thereof.

2. A compound according to claim 1, wherein $R^1$ and $R^2$ are each independently H or W.

3. A compound according to claim 1 of Formula Ia:

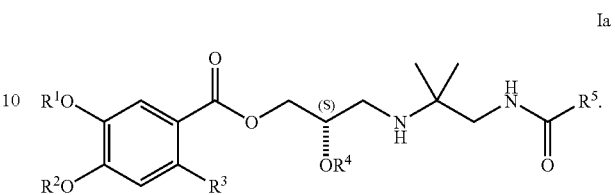

4. A compound according to claim 1, wherein $R^4$ is W.

5. A compound according to claim 4, wherein $R^1$ and $R^2$ are each H.

6. A compound according to claim 5 wherein $R^3$ is straight chain or branched $C_1$-$C_{10}$ alkyl, $R^5$ is tetrahydrofuran-3-yl, and W is:

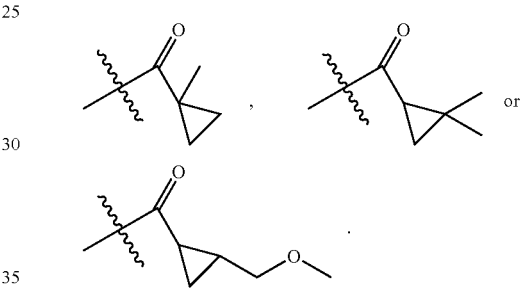

7. A compound according to claim 6 wherein W is:

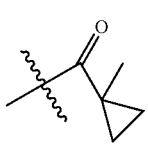

8. A compound according to claim 4 wherein $R^1$ and $R^2$ are each aralkyl.

9. A compound according to claim 8 wherein $R^4$ is:

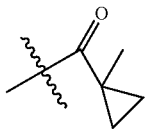

10. A compound according to claim 1, wherein at least one of the $R^6$ substituents is other than H.

11. A compound according to claim 1, wherein each $R^6$ is independently H, straight chain or branched $C_1$-$C_5$ alkyl or straight chain or branched $C_2$-$C_6$ alkoxyalkyl.

12. A compound according to claim 1, wherein each $R^6$ is independently H, methyl, or $CH_2OCH_3$.

13. A compound according to claim 1, wherein each W is independently:

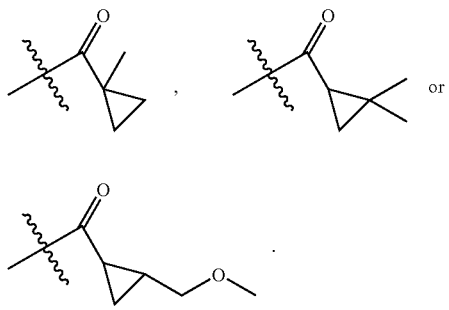

14. A compound according to claim 5, wherein each W is independently:

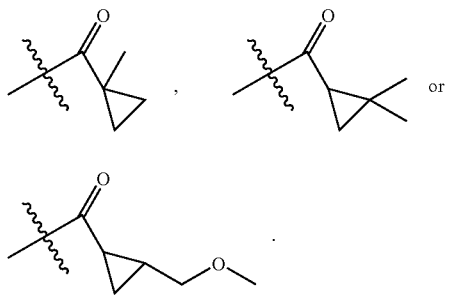

15. A compound according to claim 1 wherein $R^3$ is H or straight chain or branched $C_1$-$C_5$ alkyl.

16. A compound according to claim 1 wherein $R^3$ is methyl.

17. A compound according to claim 1, wherein $R^5$ is tetrahydrofuranyl.

18. A compound according to claim 17, wherein $R^5$ is tetrahydrofuran-3-yl.

19. A compound according to claim 3, wherein $R^5$ is tetrahydrofuran-3-yl.

20. A compound of Formula II:

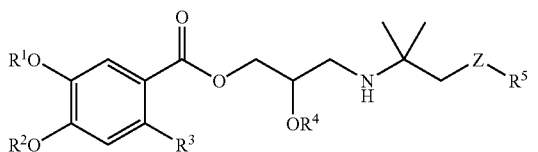

wherein:
  $R^1$ and $R^2$ are each independently H, W, or a phenoxyl protecting group;
  $R^3$ is hydrogen, straight chain or branched $C_1$-$C_{10}$ alkyl, cycloalkyl, amino, or $C_1$-$C_{10}$ alkoxy;
  $R^4$ is H or W;
  Z is —O— or —O(C=O)—;
  $R^5$ is tetrahydrofuranyl;
  W is:

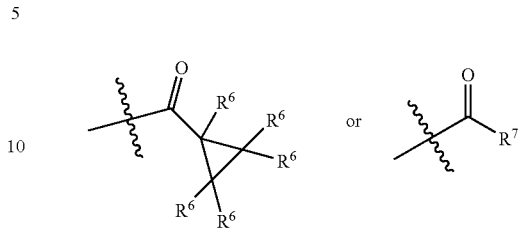

each $R^6$ is independently H, straight chain or branched $C_1$-$C_{10}$ alkyl, or straight chain or branched $C_1$-$C_{10}$ alkoxyalkyl; and
  $R^7$ is straight chain or branched alkyl, cycloalkyl, aryl, or aralkyl;
  provided that:
    when Z is —O(C=O)—, then $R^5$ is other than H;
  or a stereoisomer or pharmaceutically acceptable salt thereof.

21. A compound according to claim 20 of formula II wherein $R^4$ is H.

22. A compound according to claim 20, wherein $R^1$ and $R^2$ are each independently H or W.

23. A compound according to claim 20, wherein $R^1$, $R^2$, and $R^4$ are each H.

24. A compound according to claim 20, of Formula II(a):

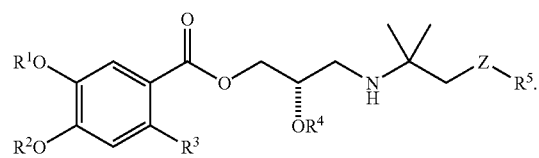

25. A compound according to claim 20, wherein $R^4$ is W.

26. A compound according to claim 25, wherein $R^1$ and $R^2$ are each H.

27. A compound according to claim 26 wherein $R^3$ is straight chain or branched $C_1$-$C_{10}$ alkyl, $R^5$ is tetrahydrofuran-3-yl, and W is:

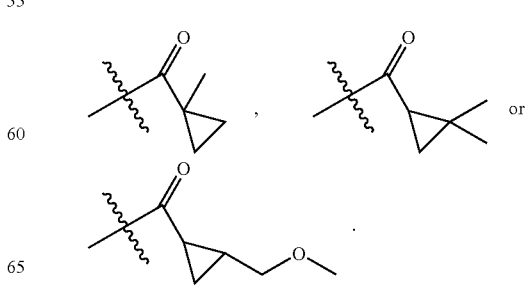

28. A compound according to claim 27 wherein W is:

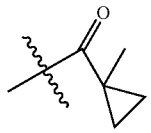

29. A compound according to claim 25 wherein $R^1$ and $R^2$ are each aralkyl.

30. A compound according to claim 25 wherein $R^4$ is:

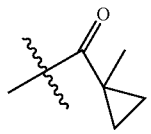

31. A compound according to claim 20, wherein at least one of the $R^6$ substituents is other than H.

32. A compound according to claim 20, wherein each $R^6$ is independently H, straight chain or branched $C_1$-$C_5$ alkyl or straight chain or branched $C_2$-$C_6$ alkoxyalkyl.

33. A compound according to claim 20, wherein each $R^6$ is independently H, methyl, or $CH_2OCH_3$.

34. A compound according to claim 20, wherein each W is independently:

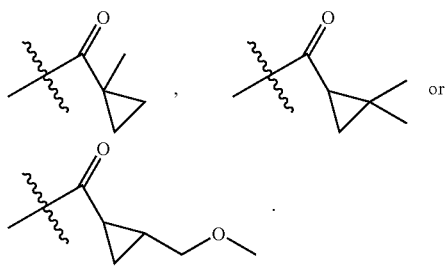

35. A compound according to claim 26, wherein each W is independently:

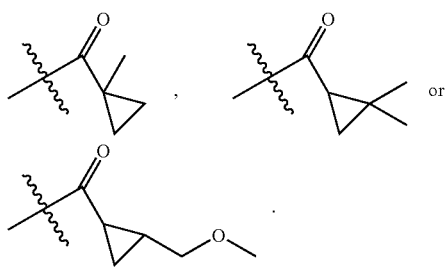

36. A compound according to claim 20 wherein $R^3$ is H or straight chain or branched $C_1$-$C_5$ alkyl.

37. A compound according to claim 20 wherein $R^3$ is methyl.

38. A compound according to claim 20, wherein $R^5$ is tetrahydrofuranyl.

39. A compound according to claim 38, wherein $R^5$ is tetrahydrofuran-3-yl.

40. A compound according to claim 20, wherein W is:

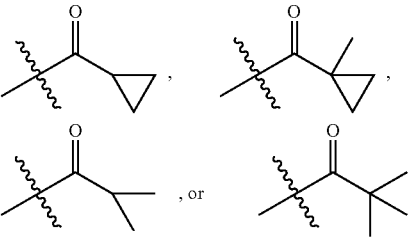

41. A compound according to claim 1, wherein $R^5$ is 3-alkyltetrahydrofuran-3-yl.

42. A compound according to claim 20, wherein $R^5$ is 3-alkyltetrahydrofuran-3-yl.

43. A compound according to claim 1, of the formula:

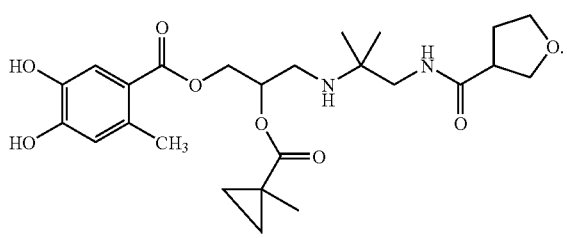

44. A compound according to claim 43, of the formula:

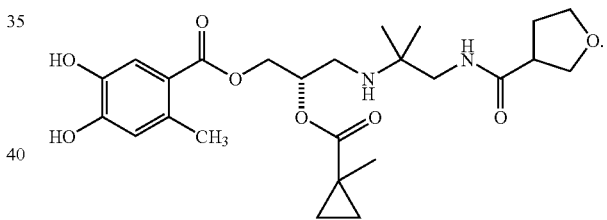

45. A pharmaceutically acceptable salt of a compound according to claim 43, of formula:

[A]·HX;

wherein A is a compound according to claim 43 and HX is an acid selected from the group consisting of hydrochloric, sulfuric, maleic, fumaric, oxalic, succinic, citric, and tartaric acids.

46. A process for producing a compound of formula IIIa:

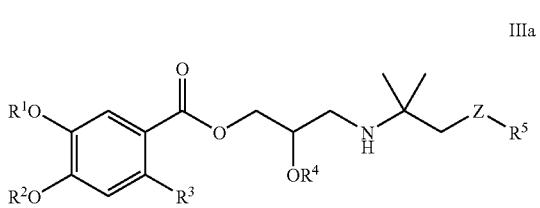

IIIa wherein:
R$^1$ and R$^2$ are each independently H, W, or a phenoxyl protecting group;

$R^3$ is hydrogen, straight chain or branched $C_1$-$C_{10}$ alkyl, cycloalkyl, amino, or $C_1$-$C_{10}$ alkoxy, $R^4$ is H or W, provided that at least one of $R^1$, $R^2$, and $R^4$ is W; and Z is —O—, —O(C=O)—, or —NH(C=O)—;

$R^5$ is tetrahydrofuranyl,

W is:

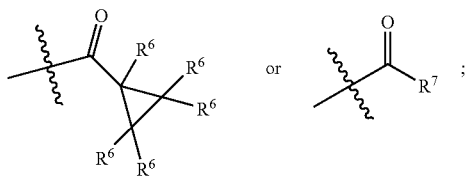

each $R^6$ is independently H, straight chain or branched $C_1$-$C_{10}$ alkyl, or straight chain or branched $C_1$-$C_{10}$ alkoxyalkyl; and $R^7$ is alkyl, cycloalkyl, aryl, or aralkyl;

provided that:
when Z is —O(C=O)—, then $R^5$ is other than H; and
when Z is —NH(C=O)—, then $R^5$ is other than H, and W is:

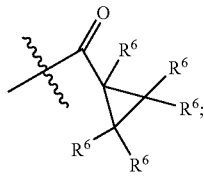

comprising contacting a compound of the formula:

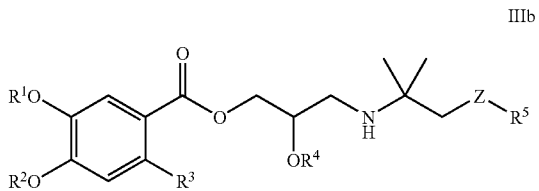

IIIb wherein:
at least one of $R^1$, $R^2$, and $R^4$ is H;
with at least one compound of formula W–L, wherein each L is independently a leaving group;
to produce a compound of formula IIIa.

47. A pharmaceutical composition for treating glaucoma, ocular hypertension, or optic neuropathy associated with the eye of a patient, the composition comprising an ophthalmologically acceptable carrier or diluent and a compound according to claim 1; or a stereoisomer or pharmaceutically acceptable salt thereof.

48. The composition according to claim 47, wherein the glaucoma, ocular hypertension, or optic neuropathy is classified as open-angle glaucoma.

49. The composition according to claim 47, formulated as an eye drop, eye wash, or eye ointment.

50. The composition according to claim 47, formulated for administration from a polymeric disk or wafer placed upon the surface of the eye.

51. A method of treating glaucoma, ocular hypertension, or optic neuropathy associated with the eye of a patient, wherein the method comprises:
administering to the eye of the patient a composition comprising an ophthalmologically acceptable carrier or diluent and a compound according to claim 1; or a stereoisomer or pharmaceutically acceptable salt thereof, in a therapeutically sufficient amount to ameliorate, delay, or reduce the symptoms of glaucoma, ocular hypertension, or optic neuropathy.

52. The method according to claim 51, wherein the glaucoma, ocular hypertension, or optic neuropathy is classified as open-angle glaucoma.

53. The method according to claim 51, wherein the composition is administered in an eye drop, eye wash, or eye ointment.

54. The method according to claim 51, wherein the composition is administered from a polymeric disk or wafer placed upon the surface of the eye.

55. A pharmaceutical composition for treating glaucoma, wherein the glaucoma, ocular hypertension, or optic neuropathy associated with the eye of a patient, the composition comprising an ophthalmologically acceptable carrier or diluent and a compound according to claim 20 or a stereoisomer, or pharmaceutically acceptable salt thereof.

56. The composition according to claim 55, wherein the glaucoma, ocular hypertension, or optic neuropathy is classified as open-angle glaucoma.

57. The composition according to claim 55, formulated as an eye drop, eye wash, or eye ointment.

58. The composition according to claim 55, formulated for administration from a polymeric disk or wafer placed upon the surface of the eye.

59. A method of treating glaucoma, wherein the glaucoma, ocular hypertension, or optic neuropathy associated with the eye of a patient, wherein the method comprises administering to the eye of the patient a composition comprising an ophthalmologically acceptable carrier or diluent and a compound according to claim 20, or a stereoisomer or pharmaceutically acceptable salt thereof, in a therapeutically sufficient amount to ameliorate, delay, or reduce the symptoms of glaucoma, wherein the glaucoma, ocular hypertension, or optic neuropathy.

60. The method according to claim 59, wherein the glaucoma, ocular hypertension, or optic neuropathy is classified as open-angle glaucoma.

61. The method according to claim 59, wherein the composition is administered in an eye drop, eye wash, or eye ointment.

62. The method according to claim 59, wherein the composition is administered from a polymeric disk or wafer placed upon the surface of the eye.

* * * * *